(12) United States Patent
Han et al.

(10) Patent No.: US 12,053,492 B2
(45) Date of Patent: Aug. 6, 2024

(54) PERINATAL TISSUE DERIVED MESENCHYMAL STEM CELLS: METHOD OF PREPARATION AND USES THEREOF

(71) Applicant: HEALTH AND BIOTECH FRANCE (H & B FRANCE), Paris (FR)

(72) Inventors: ZhongChao Han, Beijing (CN); Zhibo Han, Beijing (CN); Tao Wang, Beijing (CN)

(73) Assignee: HEALTH AND BIOTECH FRANCE (H & B FRANCE), Paris (FR)

(*) Notice: Subject to any disclaimer, the term of this patent is extended or adjusted under 35 U.S.C. 154(b) by 938 days.

(21) Appl. No.: 16/468,669

(22) PCT Filed: Dec. 12, 2017

(86) PCT No.: PCT/EP2017/082316
§ 371 (c)(1),
(2) Date: Jun. 11, 2019

(87) PCT Pub. No.: WO2018/108859
PCT Pub. Date: Jun. 21, 2018

(65) Prior Publication Data
US 2020/0009193 A1    Jan. 9, 2020

(30) Foreign Application Priority Data
Dec. 12, 2016 (WO) .................. PCT/IB2016/001936

(51) Int. Cl.
A61K 35/28 (2015.01)
A61K 9/06 (2006.01)
C12N 5/0775 (2010.01)

(52) U.S. Cl.
CPC .............. *A61K 35/28* (2013.01); *A61K 9/06* (2013.01); *C12N 5/0663* (2013.01); *C12N 2501/2301* (2013.01); *C12N 2501/2304* (2013.01); *C12N 2506/025* (2013.01)

(58) Field of Classification Search
CPC ........ A61K 35/28; A61K 9/06; C12N 5/0663; C12N 2501/2301; C12N 2501/2304; C12N 2501/025
See application file for complete search history.

(56) References Cited

U.S. PATENT DOCUMENTS

2015/0313946 A1    11/2015    Shi et al.

FOREIGN PATENT DOCUMENTS

| WO | WO2010107286 A2 * | 9/2010 | ............... A61K 8/98 |
| WO | 2014/093948 A1 | 6/2014 | |

OTHER PUBLICATIONS

Yang ZX, Han ZB, Ji YR, Wang YW, Liang L, Chi Y, Yang SG, Li LN, Luo WF, Li JP, Chen DD, Du WJ, Cao XC, Zhuo GS, Wang T, Han ZC. CD106 identifies a subpopulation of mesenchymal stem cells with unique immunomodulatory properties. PLoS One. 2013; 8(3):e59354. (Year: 2013).*
Li, Dong, et al., Biological characteristics of human placental mesenchymal stem cells and their proliferative response to various cytokines, Cells Tissues Organs, 186: 169-179. (Year: 2007).*
Abumaree et al., Phenotypic and functional characterization of mesenchymal stem cells from chorionic villi of human term placenta, Stem Cell Reviews and Reports, 9: 16-31. (Year: 2013).*
You et al., WO2010107286A2, Machine Translation, PE2E obtained Aug. 12, 2022 (Year: 2010).*
Hruza et al., Mechanisms if UV-induced inflammation, Journal of Investigative Dermatology, 100(1): p. 35S-41S. (Year: 1993).*
Lee et al., Effect of Ex Vivo Culture Conditions on Immunosuppression by Human Mesenchymal Stem Cells, BioMed Research International, p. 1-10. (Year: 2013).*
Nguyen et al., Improved Function and Myocardial Repair of Infarcted Heart by Intracoronary Injection of Mesenchymal Stem Cell-Derived Growth Factors, J. of Cardiovasc. Trans. Res., 3: 547-558. (Year: 2010).*
Yang et al., CD106 Identifies a Subpopulation of Mesenchymal Stem Cells with Unique Immunomodulatory Properties, PLOS One, 8(3): 1-12. (Year: 2013).*
Simmons et al., Vascular Cell Adhesion Molecule-1 Expressed by Bone Marrow Stromal Cells Mediates the Binding of Hematopoietic Progenitor Cells, Blood 80(2): 388-395. (Year: 1992).*

(Continued)

*Primary Examiner* — Laura Schuberg
*Assistant Examiner* — Joseph Paul Miano
(74) *Attorney, Agent, or Firm* — Arrigo, Lee, Guttman & Mouta-Bellum LLP

(57) ABSTRACT

The present invention discloses the preparation of placenta tissue derived $CD106^{high}$ CD151+Nestin+ mesenchymal stem cells (MSCs). In a first aspect, the invention relates to a particular method to prepare these cells at industrial scale and the cell population generated thereby. In a second aspect, the invention relates to a cell culture obtained by said particular method, containing placental $CD106^{high}$ CD151+Nestin+ MSCs expressing the vascular cell adhesion molecule 1 (VCAM-1) marker. The present application shows that said placental $CD106^{high}$ CD151+Nestin+ MSCs are capable of inducing angiogenesis in vitro and in vivo. The herein presented results also show that administering said placental $CD106^{high}$ CD151+Nestin+ MSCs to individuals suffering from an ischemic disease or from a disorder of the circulatory system results in a detectable improvement of one or more symptoms of said disease or disorder. Therefore, in a third aspect, the invention relates to placental $CD106^{high}$ CD151+Nestin+ MSCs for use as a medicament for treating subjects suffering from an ischemic disease, a disorder of the circulatory system, an immune disease, an organ injury or an organ function failure.

8 Claims, 6 Drawing Sheets
Specification includes a Sequence Listing.

(56) References Cited

OTHER PUBLICATIONS

Le Blanc et al., Mesenchymal stem cells inhibit and stimulate mixed lymphocyte cultures and mitogenic responses independently of the major histocompatibility complex, Scandinavian Journal of Immunology, 57: 11-20. (Year: 2003).*

Lee et al., Changes in surface markers of human mesenchymal stem cells during the chondrogenic differentiation and dedifferentiation process in vitro, Arthritis and Rheumatism, 60(8): 2325-2332. (Year: 2009).*

Masinovsky et al., IL-4 acts synergistically with IL-1 beta to promote lymphocyte adhesion to microvascular endothelium by induction of vascular cell adhesion molecule-1, Journal of Immunology, 145(9): 2886-2895. (Year: 1990).*

Fan et al., Pre-treatment with IL-1b enhances the efficacy of MSC transplantation in DSS-induced colitis, Cellular & Molecular Immunology (2012) 9, 473-481.

Savilova et al., Comparison of the Expression of Immunomodulatory Factors in Cultures of Mesenchymal Stromal Cells from Human Extraembryonic Tissues, Cell Technologies in Biology and Medicine, No. 4, Feb. 2015, 555-560.

Abomaray et al., Phenotypic and Functional Characterization of Mesenchymal Stem/Multipotent Stromal Cells from Decidua Basalis of Human Term Placenta, Stem Cells International vol. 2016, Article ID 5184601, 18 pages.

\* cited by examiner

SEQUENCE LISTING

```
<160> NUMBER OF SEQ ID NOS: 7

<210> SEQ ID NO 1
<211> LENGTH: 739
<212> TYPE: PRT
<213> ORGANISM: homo sapiens
<220> FEATURE:
<221> NAME/KEY: MISC_FEATURE
```

-continued

<223> OTHER INFORMATION: isoform a of CD106 in human

<400> SEQUENCE: 1

```
Met Pro Gly Lys Met Val Val Ile Leu Gly Ala Ser Asn Ile Leu Trp
 1               5                  10                  15
Ile Met Phe Ala Ala Ser Gln Ala Phe Lys Ile Glu Thr Thr Pro Glu
                20                  25                  30
Ser Arg Tyr Leu Ala Gln Ile Gly Asp Ser Val Ser Leu Thr Cys Ser
            35                  40                  45
Thr Thr Gly Cys Glu Ser Pro Phe Phe Ser Trp Arg Thr Gln Ile Asp
    50                  55                  60
Ser Pro Leu Asn Gly Lys Val Thr Asn Glu Gly Thr Thr Ser Thr Leu
65                  70                  75                  80
Thr Met Asn Pro Val Ser Phe Gly Asn Glu His Ser Tyr Leu Cys Thr
                85                  90                  95
Ala Thr Cys Glu Ser Arg Lys Leu Glu Lys Gly Ile Gln Val Glu Ile
            100                 105                 110
Tyr Ser Phe Pro Lys Asp Pro Glu Ile His Leu Ser Gly Pro Leu Glu
        115                 120                 125
Ala Gly Lys Pro Ile Thr Val Lys Cys Ser Val Ala Asp Val Tyr Pro
    130                 135                 140
Phe Asp Arg Leu Glu Ile Asp Leu Leu Lys Gly Asp His Leu Met Lys
145                 150                 155                 160
Ser Gln Glu Phe Leu Glu Asp Ala Asp Arg Lys Ser Leu Glu Thr Lys
                165                 170                 175
Ser Leu Glu Val Thr Phe Thr Pro Val Ile Glu Asp Ile Gly Lys Val
            180                 185                 190
Leu Val Cys Arg Ala Lys Leu His Ile Asp Glu Met Asp Ser Val Pro
        195                 200                 205
Thr Val Arg Gln Ala Val Lys Glu Leu Gln Val Tyr Ile Ser Pro Lys
    210                 215                 220
Asn Thr Val Ile Ser Val Asn Pro Ser Thr Lys Leu Gln Glu Gly Gly
225                 230                 235                 240
Ser Val Thr Met Thr Cys Ser Ser Glu Gly Leu Pro Ala Pro Glu Ile
                245                 250                 255
Phe Trp Ser Lys Lys Leu Asp Asn Gly Asn Leu Gln His Leu Ser Gly
            260                 265                 270
Asn Ala Thr Leu Thr Leu Ile Ala Met Arg Met Glu Asp Ser Gly Ile
        275                 280                 285
Tyr Val Cys Glu Gly Val Asn Leu Ile Gly Lys Asn Arg Lys Glu Val
    290                 295                 300
Glu Leu Ile Val Gln Glu Lys Pro Phe Thr Val Glu Ile Ser Pro Gly
305                 310                 315                 320
Pro Arg Ile Ala Ala Gln Ile Gly Asp Ser Val Met Leu Thr Cys Ser
                325                 330                 335
Val Met Gly Cys Glu Ser Pro Ser Phe Ser Trp Arg Thr Gln Ile Asp
            340                 345                 350
Ser Pro Leu Ser Gly Lys Val Arg Ser Glu Gly Thr Asn Ser Thr Leu
        355                 360                 365
Thr Leu Ser Pro Val Ser Phe Glu Asn Glu His Ser Tyr Leu Cys Thr
    370                 375                 380
Val Thr Cys Gly His Lys Lys Leu Glu Lys Gly Ile Gln Val Glu Leu
385                 390                 395                 400
```

```
Tyr Ser Phe Pro Arg Asp Pro Glu Ile Glu Met Ser Gly Gly Leu Val
            405                 410                 415

Asn Gly Ser Ser Val Thr Val Ser Cys Lys Val Pro Ser Val Tyr Pro
        420                 425                 430

Leu Asp Arg Leu Glu Ile Glu Leu Leu Lys Gly Glu Thr Ile Leu Glu
        435                 440                 445

Asn Ile Glu Phe Leu Glu Asp Thr Asp Met Lys Ser Leu Glu Asn Lys
450                 455                 460

Ser Leu Glu Met Thr Phe Ile Pro Thr Ile Glu Asp Thr Gly Lys Ala
465                 470                 475                 480

Leu Val Cys Gln Ala Lys Leu His Ile Asp Asp Met Glu Phe Glu Pro
                485                 490                 495

Lys Gln Arg Gln Ser Thr Gln Thr Leu Tyr Val Asn Val Ala Pro Arg
            500                 505                 510

Asp Thr Thr Val Leu Val Ser Pro Ser Ser Ile Leu Glu Glu Gly Ser
        515                 520                 525

Ser Val Asn Met Thr Cys Leu Ser Gln Gly Phe Pro Ala Pro Lys Ile
        530                 535                 540

Leu Trp Ser Arg Gln Leu Pro Asn Gly Glu Leu Gln Pro Leu Ser Glu
545                 550                 555                 560

Asn Ala Thr Leu Thr Leu Ile Ser Thr Lys Met Glu Asp Ser Gly Val
                565                 570                 575

Tyr Leu Cys Glu Gly Ile Asn Gln Ala Gly Arg Ser Arg Lys Glu Val
            580                 585                 590

Glu Leu Ile Ile Gln Val Thr Pro Lys Asp Ile Lys Leu Thr Ala Phe
        595                 600                 605

Pro Ser Glu Ser Val Lys Glu Gly Asp Thr Val Ile Ile Ser Cys Thr
    610                 615                 620

Cys Gly Asn Val Pro Glu Thr Trp Ile Ile Leu Lys Lys Lys Ala Glu
625                 630                 635                 640

Thr Gly Asp Thr Val Leu Lys Ser Ile Asp Gly Ala Tyr Thr Ile Arg
                645                 650                 655

Lys Ala Gln Leu Lys Asp Ala Gly Val Tyr Glu Cys Glu Ser Lys Asn
            660                 665                 670

Lys Val Gly Ser Gln Leu Arg Ser Leu Thr Leu Asp Val Gln Gly Arg
        675                 680                 685

Glu Asn Asn Lys Asp Tyr Phe Ser Pro Glu Leu Leu Val Leu Tyr Phe
    690                 695                 700

Ala Ser Ser Leu Ile Ile Pro Ala Ile Gly Met Ile Ile Tyr Phe Ala
705                 710                 715                 720

Arg Lys Ala Asn Met Lys Gly Ser Tyr Ser Leu Val Glu Ala Gln Lys
                725                 730                 735

Ser Lys Val

<210> SEQ ID NO 2
<211> LENGTH: 647
<212> TYPE: PRT
<213> ORGANISM: homo sapiens
<220> FEATURE:
<221> NAME/KEY: MISC_FEATURE
<223> OTHER INFORMATION: isoform b of CD106 human

<400> SEQUENCE: 2

Met Pro Gly Lys Met Val Val Ile Leu Gly Ala Ser Asn Ile Leu Trp
1               5                   10                  15
```

-continued

```
Ile Met Phe Ala Ala Ser Gln Ala Phe Lys Ile Glu Thr Thr Pro Glu
             20                  25                  30

Ser Arg Tyr Leu Ala Gln Ile Gly Asp Ser Val Ser Leu Thr Cys Ser
         35                  40                  45

Thr Thr Gly Cys Glu Ser Pro Phe Phe Ser Trp Arg Thr Gln Ile Asp
     50                  55                  60

Ser Pro Leu Asn Gly Lys Val Thr Asn Glu Gly Thr Thr Ser Thr Leu
65                  70                  75                  80

Thr Met Asn Pro Val Ser Phe Gly Asn Glu His Ser Tyr Leu Cys Thr
                 85                  90                  95

Ala Thr Cys Glu Ser Arg Lys Leu Glu Lys Gly Ile Gln Val Glu Ile
            100                 105                 110

Tyr Ser Phe Pro Lys Asp Pro Glu Ile His Leu Ser Gly Pro Leu Glu
        115                 120                 125

Ala Gly Lys Pro Ile Thr Val Lys Cys Ser Val Ala Asp Val Tyr Pro
    130                 135                 140

Phe Asp Arg Leu Glu Ile Asp Leu Leu Lys Gly Asp His Leu Met Lys
145                 150                 155                 160

Ser Gln Glu Phe Leu Glu Asp Ala Asp Arg Lys Ser Leu Glu Thr Lys
                165                 170                 175

Ser Leu Glu Val Thr Phe Thr Pro Val Ile Glu Asp Ile Gly Lys Val
            180                 185                 190

Leu Val Cys Arg Ala Lys Leu His Ile Asp Glu Met Asp Ser Val Pro
        195                 200                 205

Thr Val Arg Gln Ala Val Lys Glu Leu Gln Val Tyr Ile Ser Pro Lys
    210                 215                 220

Asn Thr Val Ile Ser Val Asn Pro Ser Thr Lys Leu Gln Glu Gly Gly
225                 230                 235                 240

Ser Val Thr Met Thr Cys Ser Ser Glu Gly Leu Pro Ala Pro Glu Ile
                245                 250                 255

Phe Trp Ser Lys Lys Leu Asp Asn Gly Asn Leu Gln His Leu Ser Gly
            260                 265                 270

Asn Ala Thr Leu Thr Leu Ile Ala Met Arg Met Glu Asp Ser Gly Ile
        275                 280                 285

Tyr Val Cys Glu Gly Val Asn Leu Ile Gly Lys Asn Arg Lys Glu Val
    290                 295                 300

Glu Leu Ile Val Gln Ala Phe Pro Arg Asp Pro Glu Ile Glu Met Ser
305                 310                 315                 320

Gly Gly Leu Val Asn Gly Ser Ser Val Thr Val Ser Cys Lys Val Pro
                325                 330                 335

Ser Val Tyr Pro Leu Asp Arg Leu Glu Ile Glu Leu Leu Lys Gly Glu
            340                 345                 350

Thr Ile Leu Glu Asn Ile Glu Phe Leu Glu Asp Thr Asp Met Lys Ser
        355                 360                 365

Leu Glu Asn Lys Ser Leu Glu Met Thr Phe Ile Pro Thr Ile Glu Asp
    370                 375                 380

Thr Gly Lys Ala Leu Val Cys Gln Ala Lys Leu His Ile Asp Asp Met
385                 390                 395                 400

Glu Phe Glu Pro Lys Gln Arg Gln Ser Thr Gln Thr Leu Tyr Val Asn
                405                 410                 415

Val Ala Pro Arg Asp Thr Thr Val Leu Val Ser Pro Ser Ser Ile Leu
            420                 425                 430

Glu Glu Gly Ser Ser Val Asn Met Thr Cys Leu Ser Gln Gly Phe Pro
```

```
                435                 440                 445
Ala Pro Lys Ile Leu Trp Ser Arg Gln Leu Pro Asn Gly Glu Leu Gln
450                 455                 460

Pro Leu Ser Glu Asn Ala Thr Leu Thr Leu Ile Ser Thr Lys Met Glu
465                 470                 475                 480

Asp Ser Gly Val Tyr Leu Cys Glu Gly Ile Asn Gln Ala Gly Arg Ser
                485                 490                 495

Arg Lys Glu Val Glu Leu Ile Ile Gln Val Thr Pro Lys Asp Ile Lys
                500                 505                 510

Leu Thr Ala Phe Pro Ser Glu Ser Val Lys Glu Gly Asp Thr Val Ile
                515                 520                 525

Ile Ser Cys Thr Cys Gly Asn Val Pro Glu Thr Trp Ile Ile Leu Lys
            530                 535                 540

Lys Lys Ala Glu Thr Gly Asp Thr Val Leu Lys Ser Ile Asp Gly Ala
545                 550                 555                 560

Tyr Thr Ile Arg Lys Ala Gln Leu Lys Asp Ala Gly Val Tyr Glu Cys
                565                 570                 575

Glu Ser Lys Asn Lys Val Gly Ser Gln Leu Arg Ser Leu Thr Leu Asp
                580                 585                 590

Val Gln Gly Arg Glu Asn Asn Lys Asp Tyr Phe Ser Pro Glu Leu Leu
                595                 600                 605

Val Leu Tyr Phe Ala Ser Ser Leu Ile Ile Pro Ala Ile Gly Met Ile
            610                 615                 620

Ile Tyr Phe Ala Arg Lys Ala Asn Met Lys Gly Ser Tyr Ser Leu Val
625                 630                 635                 640

Glu Ala Gln Lys Ser Lys Val
                645

<210> SEQ ID NO 3
<211> LENGTH: 677
<212> TYPE: PRT
<213> ORGANISM: homo sapiens
<220> FEATURE:
<221> NAME/KEY: MISC_FEATURE
<223> OTHER INFORMATION: isoform c of CD106 human

<400> SEQUENCE: 3

Met Pro Gly Lys Met Val Val Ile Leu Gly Ala Ser Asn Ile Leu Trp
1               5                   10                  15

Ile Met Phe Ala Ala Ser Gln Ala Phe Lys Ile Glu Thr Thr Pro Glu
                20                  25                  30

Ser Arg Tyr Leu Ala Gln Ile Gly Asp Ser Val Ser Leu Thr Cys Ser
                35                  40                  45

Thr Thr Gly Ser Phe Pro Lys Asp Pro Glu Ile His Leu Ser Gly Pro
            50                  55                  60

Leu Glu Ala Gly Lys Pro Ile Thr Val Lys Cys Ser Val Ala Asp Val
65                  70                  75                  80

Tyr Pro Phe Asp Arg Leu Glu Ile Asp Leu Leu Lys Gly Asp His Leu
                85                  90                  95

Met Lys Ser Gln Glu Phe Leu Glu Asp Ala Asp Arg Lys Ser Leu Glu
                100                 105                 110

Thr Lys Ser Leu Glu Val Thr Phe Thr Pro Val Ile Glu Asp Ile Gly
                115                 120                 125

Lys Val Leu Val Cys Arg Ala Lys Leu His Ile Asp Glu Met Asp Ser
            130                 135                 140
```

-continued

```
Val Pro Thr Val Arg Gln Ala Val Lys Glu Leu Gln Val Tyr Ile Ser
145                 150                 155                 160

Pro Lys Asn Thr Val Ile Ser Val Asn Pro Ser Thr Lys Leu Gln Glu
                165                 170                 175

Gly Gly Ser Val Thr Met Thr Cys Ser Ser Glu Gly Leu Pro Ala Pro
            180                 185                 190

Glu Ile Phe Trp Ser Lys Lys Leu Asp Asn Gly Asn Leu Gln His Leu
        195                 200                 205

Ser Gly Asn Ala Thr Leu Thr Leu Ile Ala Met Arg Met Glu Asp Ser
210                 215                 220

Gly Ile Tyr Val Cys Glu Gly Val Asn Leu Ile Gly Lys Asn Arg Lys
225                 230                 235                 240

Glu Val Glu Leu Ile Val Gln Glu Lys Pro Phe Thr Val Glu Ile Ser
                245                 250                 255

Pro Gly Pro Arg Ile Ala Ala Gln Ile Gly Asp Ser Val Met Leu Thr
                260                 265                 270

Cys Ser Val Met Gly Cys Glu Ser Pro Ser Phe Ser Trp Arg Thr Gln
            275                 280                 285

Ile Asp Ser Pro Leu Ser Gly Lys Val Arg Ser Glu Gly Thr Asn Ser
        290                 295                 300

Thr Leu Thr Leu Ser Pro Val Ser Phe Glu Asn Glu His Ser Tyr Leu
305                 310                 315                 320

Cys Thr Val Thr Cys Gly His Lys Lys Leu Glu Lys Gly Ile Gln Val
                325                 330                 335

Glu Leu Tyr Ser Phe Pro Arg Asp Pro Glu Ile Glu Met Ser Gly Gly
            340                 345                 350

Leu Val Asn Gly Ser Ser Val Thr Val Ser Cys Lys Val Pro Ser Val
        355                 360                 365

Tyr Pro Leu Asp Arg Leu Glu Ile Glu Leu Leu Lys Gly Glu Thr Ile
370                 375                 380

Leu Glu Asn Ile Glu Phe Leu Glu Asp Thr Asp Met Lys Ser Leu Glu
385                 390                 395                 400

Asn Lys Ser Leu Glu Met Thr Phe Ile Pro Thr Ile Glu Asp Thr Gly
                405                 410                 415

Lys Ala Leu Val Cys Gln Ala Lys Leu His Ile Asp Asp Met Glu Phe
                420                 425                 430

Glu Pro Lys Gln Arg Gln Ser Thr Gln Thr Leu Tyr Val Asn Val Ala
            435                 440                 445

Pro Arg Asp Thr Thr Val Leu Val Ser Pro Ser Ser Ile Leu Glu Glu
        450                 455                 460

Gly Ser Ser Val Asn Met Thr Cys Leu Ser Gln Gly Phe Pro Ala Pro
465                 470                 475                 480

Lys Ile Leu Trp Ser Arg Gln Leu Pro Asn Gly Glu Leu Gln Pro Leu
                485                 490                 495

Ser Glu Asn Ala Thr Leu Thr Leu Ile Ser Thr Lys Met Glu Asp Ser
                500                 505                 510

Gly Val Tyr Leu Cys Glu Gly Ile Asn Gln Ala Gly Arg Ser Arg Lys
            515                 520                 525

Glu Val Glu Leu Ile Ile Gln Val Thr Pro Lys Asp Ile Lys Leu Thr
        530                 535                 540

Ala Phe Pro Ser Glu Ser Val Lys Glu Gly Asp Thr Val Ile Ile Ser
545                 550                 555                 560

Cys Thr Cys Gly Asn Val Pro Glu Thr Trp Ile Ile Leu Lys Lys Lys
```

-continued

```
                    565                 570                 575
Ala Glu Thr Gly Asp Thr Val Leu Lys Ser Ile Asp Gly Ala Tyr Thr
                580                 585                 590

Ile Arg Lys Ala Gln Leu Lys Asp Ala Gly Val Tyr Glu Cys Glu Ser
                595                 600                 605

Lys Asn Lys Val Gly Ser Gln Leu Arg Ser Leu Thr Leu Asp Val Gln
            610                 615                 620

Gly Arg Glu Asn Asn Lys Asp Tyr Phe Ser Pro Glu Leu Leu Val Leu
625                 630                 635                 640

Tyr Phe Ala Ser Ser Leu Ile Ile Pro Ala Ile Gly Met Ile Ile Tyr
                645                 650                 655

Phe Ala Arg Lys Ala Asn Met Lys Gly Ser Tyr Ser Leu Val Glu Ala
                660                 665                 670

Gln Lys Ser Lys Val
                675

<210> SEQ ID NO 4
<211> LENGTH: 1621
<212> TYPE: PRT
<213> ORGANISM: homo sapiens
<220> FEATURE:
<221> NAME/KEY: MISC_FEATURE
<223> OTHER INFORMATION: Nestin human

<400> SEQUENCE: 4

Met Glu Gly Cys Met Gly Glu Glu Ser Phe Gln Met Trp Glu Leu Asn
1               5                   10                  15

Arg Arg Leu Glu Ala Tyr Leu Ala Arg Val Lys Ala Leu Glu Glu Gln
                20                  25                  30

Asn Glu Leu Leu Ser Ala Glu Leu Gly Gly Leu Arg Ala Gln Ser Ala
            35                  40                  45

Asp Thr Ser Trp Arg Ala His Ala Asp Asp Glu Leu Ala Ala Leu Arg
        50                  55                  60

Ala Leu Val Asp Gln Arg Trp Arg Glu Lys His Ala Ala Glu Val Ala
65                  70                  75                  80

Arg Asp Asn Leu Ala Glu Glu Leu Glu Gly Val Ala Gly Arg Cys Gln
                85                  90                  95

Gln Leu Arg Leu Ala Arg Glu Arg Thr Thr Glu Glu Val Ala Arg Asn
                100                 105                 110

Arg Arg Ala Val Glu Ala Glu Lys Cys Ala Arg Ala Trp Leu Ser Ser
            115                 120                 125

Gln Val Ala Glu Leu Glu Arg Glu Leu Glu Ala Leu Arg Val Ala His
        130                 135                 140

Glu Glu Glu Arg Val Gly Leu Asn Ala Gln Ala Ala Cys Ala Pro Arg
145                 150                 155                 160

Cys Pro Ala Pro Pro Arg Gly Pro Ala Pro Ala Pro Glu Val Glu
                165                 170                 175

Glu Leu Ala Arg Arg Leu Gly Glu Ala Trp Arg Gly Ala Val Arg Gly
                180                 185                 190

Tyr Gln Glu Arg Val Ala His Met Glu Thr Ser Leu Gly Gln Ala Arg
            195                 200                 205

Glu Arg Leu Gly Arg Ala Val Gln Gly Ala Arg Glu Gly Arg Leu Glu
        210                 215                 220

Leu Gln Gln Leu Gln Ala Glu Arg Gly Gly Leu Leu Glu Arg Arg Ala
225                 230                 235                 240
```

```
Ala Leu Glu Gln Arg Leu Glu Gly Arg Trp Gln Glu Arg Leu Arg Ala
            245                 250                 255
Thr Glu Lys Phe Gln Leu Ala Val Glu Ala Leu Glu Gln Glu Lys Gln
        260                 265                 270
Gly Leu Gln Ser Gln Ile Ala Gln Val Leu Glu Gly Arg Gln Gln Leu
    275                 280                 285
Ala His Leu Lys Met Ser Leu Ser Leu Glu Val Ala Thr Tyr Arg Thr
290                 295                 300
Leu Leu Glu Ala Glu Asn Ser Arg Leu Gln Thr Pro Gly Gly Gly Ser
305                 310                 315                 320
Lys Thr Ser Leu Ser Phe Gln Asp Pro Lys Leu Glu Leu Gln Phe Pro
                325                 330                 335
Arg Thr Pro Glu Gly Arg Arg Leu Gly Ser Leu Leu Pro Val Leu Ser
            340                 345                 350
Pro Thr Ser Leu Pro Ser Pro Leu Pro Ala Thr Leu Glu Thr Pro Val
        355                 360                 365
Pro Ala Phe Leu Lys Asn Gln Glu Phe Leu Gln Ala Arg Thr Pro Thr
    370                 375                 380
Leu Ala Ser Thr Pro Ile Pro Pro Thr Pro Gln Ala Pro Ser Pro Ala
385                 390                 395                 400
Val Asp Ala Glu Ile Arg Ala Gln Asp Ala Pro Leu Ser Leu Leu Gln
                405                 410                 415
Thr Gln Gly Gly Arg Lys Gln Ala Pro Glu Pro Leu Arg Ala Glu Ala
            420                 425                 430
Arg Val Ala Ile Pro Ala Ser Val Leu Pro Gly Pro Glu Glu Pro Gly
        435                 440                 445
Gly Gln Arg Gln Glu Ala Ser Thr Gly Gln Ser Pro Glu Asp His Ala
    450                 455                 460
Ser Leu Ala Pro Pro Leu Ser Pro Asp His Ser Ser Leu Glu Ala Lys
465                 470                 475                 480
Asp Gly Glu Ser Gly Ser Arg Val Phe Ser Ile Cys Arg Gly Glu
                485                 490                 495
Gly Glu Gly Gln Ile Trp Gly Leu Val Glu Lys Glu Thr Ala Ile Glu
            500                 505                 510
Gly Lys Val Val Ser Ser Leu Gln Gln Glu Ile Trp Glu Glu Glu Asp
        515                 520                 525
Leu Asn Arg Lys Glu Ile Gln Asp Ser Gln Val Pro Leu Glu Lys Glu
    530                 535                 540
Thr Leu Lys Ser Leu Gly Glu Glu Ile Gln Glu Ser Leu Lys Thr Leu
545                 550                 555                 560
Glu Asn Gln Ser His Glu Thr Leu Glu Arg Glu Asn Gln Glu Cys Pro
                565                 570                 575
Arg Ser Leu Glu Glu Asp Leu Glu Thr Leu Lys Ser Leu Glu Lys Glu
            580                 585                 590
Asn Lys Glu Leu Leu Lys Asp Val Glu Val Val Arg Pro Leu Glu Lys
        595                 600                 605
Glu Ala Val Gly Gln Leu Lys Pro Thr Gly Lys Glu Asp Thr Gln Thr
    610                 615                 620
Leu Gln Ser Leu Gln Lys Glu Asn Gln Glu Leu Met Lys Ser Leu Glu
625                 630                 635                 640
Gly Asn Leu Glu Thr Phe Leu Phe Pro Gly Thr Glu Asn Gln Glu Leu
                645                 650                 655
Val Ser Ser Leu Gln Glu Asn Leu Glu Ser Leu Thr Ala Leu Glu Lys
```

```
              660              665              670
Glu Asn Gln Glu Pro Leu Arg Ser Pro Glu Val Gly Asp Glu Glu Ala
            675              680              685

Leu Arg Pro Leu Thr Lys Glu Asn Gln Glu Pro Leu Arg Ser Leu Glu
690              695              700

Asp Glu Asn Lys Glu Ala Phe Arg Ser Leu Glu Lys Glu Asn Gln Glu
705              710              715              720

Pro Leu Lys Thr Leu Glu Glu Asp Gln Ser Ile Val Arg Pro Leu
            725              730              735

Glu Thr Glu Asn His Lys Ser Leu Arg Ser Leu Glu Glu Gln Asp Gln
            740              745              750

Glu Thr Leu Arg Thr Leu Glu Lys Glu Thr Gln Gln Arg Arg Arg Ser
            755              760              765

Leu Gly Glu Gln Asp Gln Met Thr Leu Arg Pro Pro Glu Lys Val Asp
            770              775              780

Leu Glu Pro Leu Lys Ser Leu Asp Gln Glu Ile Ala Arg Pro Leu Glu
785              790              795              800

Asn Glu Asn Gln Glu Phe Leu Lys Ser Leu Lys Glu Ser Val Glu
            805              810              815

Ala Val Lys Ser Leu Glu Thr Glu Ile Leu Glu Ser Leu Lys Ser Ala
            820              825              830

Gly Gln Glu Asn Leu Glu Thr Leu Lys Ser Pro Glu Thr Gln Ala Pro
            835              840              845

Leu Trp Thr Pro Glu Glu Ile Asn Gln Gly Ala Met Asn Pro Leu Glu
850              855              860

Lys Glu Ile Gln Glu Pro Leu Glu Ser Val Glu Val Asn Gln Glu Thr
865              870              875              880

Phe Arg Leu Leu Glu Glu Asn Gln Glu Ser Leu Arg Ser Leu Gly
            885              890              895

Ala Trp Asn Leu Glu Asn Leu Arg Ser Pro Glu Glu Val Asp Lys Glu
            900              905              910

Ser Gln Arg Asn Leu Glu Glu Glu Asn Leu Gly Lys Gly Glu Tyr
915              920              925

Gln Glu Ser Leu Arg Ser Leu Glu Glu Gly Gln Glu Leu Pro Gln
            930              935              940

Ser Ala Asp Val Gln Arg Trp Glu Asp Thr Val Glu Lys Asp Gln Glu
945              950              955              960

Leu Ala Gln Glu Ser Pro Pro Gly Met Ala Gly Val Glu Asn Glu Asp
            965              970              975

Glu Ala Glu Leu Asn Leu Arg Glu Gln Asp Gly Phe Thr Gly Lys Glu
            980              985              990

Glu Val Val Glu Gln Gly Glu Leu Asn Ala Thr Glu Glu Val Trp Ile
            995              1000             1005

Pro Gly Glu Gly His Pro Glu Ser Pro Glu Pro Lys Glu Gln Arg
            1010             1015             1020

Gly Leu Val Glu Gly Ala Ser Val Lys Gly Gly Ala Glu Gly Leu
            1025             1030             1035

Gln Asp Pro Glu Gly Gln Ser Gln Gln Val Gly Ala Pro Gly Leu
            1040             1045             1050

Gln Ala Pro Gln Gly Leu Pro Glu Ala Ile Glu Pro Leu Val Glu
            1055             1060             1065

Asp Asp Val Ala Pro Gly Gly Asp Gln Ala Ser Pro Glu Val Met
            1070             1075             1080
```

-continued

```
Leu Gly Ser Glu Pro Ala Met Gly Glu Ser Ala Ala Gly Ala Glu
    1085            1090            1095

Pro Gly Pro Gly Gln Gly Val Gly Gly Leu Gly Asp Pro Gly His
    1100            1105            1110

Leu Thr Arg Glu Glu Val Met Glu Pro Pro Leu Glu Glu Ser
    1115            1120            1125

Leu Glu Ala Lys Arg Val Gln Gly Leu Glu Gly Pro Arg Lys Asp
    1130            1135            1140

Leu Glu Glu Ala Gly Gly Leu Gly Thr Glu Phe Ser Glu Leu Pro
    1145            1150            1155

Gly Lys Ser Arg Asp Pro Trp Glu Pro Arg Glu Gly Arg Glu
    1160            1165            1170

Glu Ser Glu Ala Glu Ala Pro Arg Gly Ala Glu Ala Phe Pro
    1175            1180            1185

Ala Glu Thr Leu Gly His Thr Gly Ser Asp Ala Pro Ser Pro Trp
    1190            1195            1200

Pro Leu Gly Ser Glu Glu Ala Glu Glu Asp Val Pro Pro Val Leu
    1205            1210            1215

Val Ser Pro Ser Pro Thr Tyr Thr Pro Ile Leu Glu Asp Ala Pro
    1220            1225            1230

Gly Pro Gln Pro Gln Ala Glu Gly Ser Gln Glu Ala Ser Trp Gly
    1235            1240            1245

Val Gln Gly Arg Ala Glu Ala Leu Gly Lys Val Glu Ser Glu Gln
    1250            1255            1260

Glu Glu Leu Gly Ser Gly Glu Ile Pro Glu Gly Pro Gln Glu Glu
    1265            1270            1275

Gly Glu Glu Ser Arg Glu Glu Ser Glu Glu Asp Glu Leu Gly Glu
    1280            1285            1290

Thr Leu Pro Asp Ser Thr Pro Leu Gly Phe Tyr Leu Arg Ser Pro
    1295            1300            1305

Thr Ser Pro Arg Trp Asp Pro Thr Gly Glu Gln Arg Pro Pro Pro
    1310            1315            1320

Gln Gly Glu Thr Gly Lys Glu Gly Trp Asp Pro Ala Val Leu Ala
    1325            1330            1335

Ser Glu Gly Leu Glu Ala Pro Pro Ser Glu Lys Glu Glu Gly Glu
    1340            1345            1350

Glu Gly Glu Glu Glu Cys Gly Arg Asp Ser Asp Leu Ser Glu Glu
    1355            1360            1365

Phe Glu Asp Leu Gly Thr Glu Ala Pro Phe Leu Pro Gly Val Pro
    1370            1375            1380

Gly Glu Val Ala Glu Pro Leu Gly Gln Val Pro Gln Leu Leu Leu
    1385            1390            1395

Asp Pro Ala Ala Trp Asp Arg Asp Gly Glu Ser Asp Gly Phe Ala
    1400            1405            1410

Asp Glu Glu Glu Ser Gly Glu Glu Gly Glu Glu Asp Gln Glu Glu
    1415            1420            1425

Gly Arg Glu Pro Gly Ala Gly Arg Trp Gly Pro Gly Ser Ser Val
    1430            1435            1440

Gly Ser Leu Gln Ala Leu Ser Ser Ser Gln Arg Gly Glu Phe Leu
    1445            1450            1455

Glu Ser Asp Ser Val Ser Val Ser Val Pro Trp Asp Asp Ser Leu
    1460            1465            1470
```

```
Arg Gly Ala Val Ala Gly Ala Pro Lys Thr Ala Leu Glu Thr Glu
    1475            1480                1485

Ser Gln Asp Ser Ala Glu Pro Ser Gly Ser Glu Glu Glu Ser Asp
    1490            1495                1500

Pro Val Ser Leu Glu Arg Glu Asp Lys Val Pro Gly Pro Leu Glu
    1505            1510                1515

Ile Pro Ser Gly Met Glu Asp Ala Gly Pro Gly Ala Asp Ile Ile
    1520            1525                1530

Gly Val Asn Gly Gln Gly Pro Asn Leu Glu Gly Lys Ser Gln His
    1535            1540                1545

Val Asn Gly Gly Val Met Asn Gly Leu Glu Gln Ser Glu Glu Val
    1550            1555                1560

Gly Gln Gly Met Pro Leu Val Ser Glu Gly Asp Arg Gly Ser Pro
    1565            1570                1575

Phe Gln Glu Glu Glu Gly Ser Ala Leu Lys Thr Ser Trp Ala Gly
    1580            1585                1590

Ala Pro Val His Leu Gly Gln Gly Gln Phe Leu Lys Phe Thr Gln
    1595            1600                1605

Arg Glu Gly Asp Arg Glu Ser Trp Ser Ser Gly Glu Asp
    1610            1615                1620

<210> SEQ ID NO 5
<211> LENGTH: 253
<212> TYPE: PRT
<213> ORGANISM: homo sapiens
<220> FEATURE:
<221> NAME/KEY: MISC_FEATURE
<223> OTHER INFORMATION: CD151 human

<400> SEQUENCE: 5

Met Gly Glu Phe Asn Glu Lys Lys Thr Thr Cys Gly Thr Val Cys Leu
1               5                   10                  15

Lys Tyr Leu Leu Phe Thr Tyr Asn Cys Cys Phe Trp Leu Ala Gly Leu
            20                  25                  30

Ala Val Met Ala Val Gly Ile Trp Thr Leu Ala Leu Lys Ser Asp Tyr
        35                  40                  45

Ile Ser Leu Leu Ala Ser Gly Thr Tyr Leu Ala Thr Ala Tyr Ile Leu
    50                  55                  60

Val Val Ala Gly Thr Val Val Met Val Thr Gly Val Leu Gly Cys Cys
65                  70                  75                  80

Ala Thr Phe Lys Glu Arg Arg Asn Leu Leu Arg Leu Tyr Phe Ile Leu
                85                  90                  95

Leu Leu Ile Ile Phe Leu Leu Glu Ile Ile Ala Gly Ile Leu Ala Tyr
            100                 105                 110

Ala Tyr Tyr Gln Gln Leu Asn Thr Glu Leu Lys Glu Asn Leu Lys Asp
        115                 120                 125

Thr Met Thr Lys Arg Tyr His Gln Pro Gly His Glu Ala Val Thr Ser
    130                 135                 140

Ala Val Asp Gln Leu Gln Gln Glu Phe His Cys Cys Gly Ser Asn Asn
145                 150                 155                 160

Ser Gln Asp Trp Arg Asp Ser Glu Trp Ile Arg Ser Gln Glu Ala Gly
                165                 170                 175

Gly Arg Val Val Pro Asp Ser Cys Cys Lys Thr Val Val Ala Leu Cys
            180                 185                 190

Gly Gln Arg Asp His Ala Ser Asn Ile Tyr Lys Val Glu Gly Gly Cys
        195                 200                 205
```

```
Ile Thr Lys Leu Glu Thr Phe Ile Gln Glu His Leu Arg Val Ile Gly
        210                 215                 220
Ala Val Gly Ile Gly Ile Ala Cys Val Gln Val Phe Gly Met Ile Phe
225                 230                 235                 240
Thr Cys Cys Leu Tyr Arg Ser Leu Lys Leu Glu His Tyr
                245                 250

<210> SEQ ID NO 6
<211> LENGTH: 269
<212> TYPE: PRT
<213> ORGANISM: homo sapiens
<220> FEATURE:
<221> NAME/KEY: MISC_FEATURE
<223> OTHER INFORMATION: IL1beta human

<400> SEQUENCE: 6

Met Ala Glu Val Pro Glu Leu Ala Ser Glu Met Met Ala Tyr Tyr Ser
1               5                   10                  15
Gly Asn Glu Asp Asp Leu Phe Phe Glu Ala Asp Gly Pro Lys Gln Met
            20                  25                  30
Lys Cys Ser Phe Gln Asp Leu Asp Leu Cys Pro Leu Asp Gly Gly Ile
        35                  40                  45
Gln Leu Arg Ile Ser Asp His His Tyr Ser Lys Gly Phe Arg Gln Ala
    50                  55                  60
Ala Ser Val Val Val Ala Met Asp Lys Leu Arg Lys Met Leu Val Pro
65                  70                  75                  80
Cys Pro Gln Thr Phe Gln Glu Asn Asp Leu Ser Thr Phe Phe Pro Phe
                85                  90                  95
Ile Phe Glu Glu Glu Pro Ile Phe Phe Asp Thr Trp Asp Asn Glu Ala
            100                 105                 110
Tyr Val His Asp Ala Pro Val Arg Ser Leu Asn Cys Thr Leu Arg Asp
        115                 120                 125
Ser Gln Gln Lys Ser Leu Val Met Ser Gly Pro Tyr Glu Leu Lys Ala
    130                 135                 140
Leu His Leu Gln Gly Gln Asp Met Glu Gln Gln Val Val Phe Ser Met
145                 150                 155                 160
Ser Phe Val Gln Gly Glu Glu Ser Asn Asp Lys Ile Pro Val Ala Leu
                165                 170                 175
Gly Leu Lys Glu Lys Asn Leu Tyr Leu Ser Cys Val Leu Lys Asp Asp
            180                 185                 190
Lys Pro Thr Leu Gln Leu Glu Ser Val Asp Pro Lys Asn Tyr Pro Lys
        195                 200                 205
Lys Lys Met Glu Lys Arg Phe Val Phe Asn Lys Ile Glu Ile Asn Asn
    210                 215                 220
Lys Leu Glu Phe Glu Ser Ala Gln Phe Pro Asn Trp Tyr Ile Ser Thr
225                 230                 235                 240
Ser Gln Ala Glu Asn Met Pro Val Phe Leu Gly Gly Thr Lys Gly Gly
                245                 250                 255
Gln Asp Ile Thr Asp Phe Thr Met Gln Phe Val Ser Ser
            260                 265

<210> SEQ ID NO 7
<211> LENGTH: 153
<212> TYPE: PRT
<213> ORGANISM: homo sapiens
<220> FEATURE:
<221> NAME/KEY: MISC_FEATURE
```

```
<223> OTHER INFORMATION: IL4 human

<400> SEQUENCE: 7

Met Gly Leu Thr Ser Gln Leu Leu Pro Pro Leu Phe Phe Leu Leu Ala
1               5                   10                  15

Cys Ala Gly Asn Phe Val His Gly His Lys Cys Asp Ile Thr Leu Gln
            20                  25                  30

Glu Ile Ile Lys Thr Leu Asn Ser Leu Thr Glu Gln Lys Thr Leu Cys
        35                  40                  45

Thr Glu Leu Thr Val Thr Asp Ile Phe Ala Ala Ser Lys Asn Thr Thr
    50                  55                  60

Glu Lys Glu Thr Phe Cys Arg Ala Ala Thr Val Leu Arg Gln Phe Tyr
65                  70                  75                  80

Ser His His Glu Lys Asp Thr Arg Cys Leu Gly Ala Thr Ala Gln Gln
                85                  90                  95

Phe His Arg His Lys Gln Leu Ile Arg Phe Leu Lys Arg Leu Asp Arg
            100                 105                 110

Asn Leu Trp Gly Leu Ala Gly Leu Asn Ser Cys Pro Val Lys Glu Ala
        115                 120                 125

Asn Gln Ser Thr Leu Glu Asn Phe Leu Glu Arg Leu Lys Thr Ile Met
    130                 135                 140

Arg Glu Lys Tyr Ser Lys Cys Ser Ser
145                 150
```

PERINATAL TISSUE DERIVED MESENCHYMAL STEM CELLS: METHOD OF PREPARATION AND USES THEREOF

BACKGROUND OF THE INVENTION

Mesenchymal stem cells (MSCs) are known to be useful in regenerative medicine and tissue engineering. In adults, bone marrow, adipose tissue, dental pulp, and menstrual blood are the main sources of MSCs. They can also be obtained by cultivating placental cells or umbilical cord cells for 3-4 weeks in FCS-supplemented DMEM ([12], [13], [14]).

MSCs have a mesodermal, ectodermal and endodermal differentiation potential. MSCs also have immunosuppressive properties. MSCs inhibit or halt maturation of dendritic cells and proliferation of T cells, B cells and NK cells. Their immunomodulatory action is mediated by the cytokines and chemokines they secrete. Several groups have demonstrated that MSCs within placental tissue display multi-lineage developmental plasticity in vitro and in vivo. Placental tissue (including umbilical cord, umbilical cord blood, placenta, chorion, amnion and amnion fluid)-derived MSCs show positive expression of CD29, CD44, CD73, CD90 and CD105, negative expression for hematopoietic surface markers CD11b, CD19, CD34 and CD45, and negative expression for the endothelial surface marker CD31. In addition, placental tissue-derived MSCs are able to trans-differentiate into cells of all three germ layers in appropriate conditions (e.g. a complete media).

Perinatal tissue-derived MSCs have also been shown to possess broad immunoregulatory capabilities and are capable of influencing both adaptive and innate immune responses. These MSCs inhibit immune cells proliferation and maturation and suppress immune reactions both in vitro and in vivo in a non-MHC restricted manner. Therefore, these MSCs are considered to be hypoimmunogenic, displaying low expression levels of HLA class I, no expression of HLA class II, and no expression of costimulatory molecules, including CD40, CD80, and CD86. Basically, these MSCs could exert widespread immunomodulatory effects on cells of both the innate and adaptive immune system. Ex-vivo expanded placenta MSCs have also been showed to suppress the activity of a broad range of immune cells, including T cells, natural killer T (NKT) cells, dendritic cells (DCs), B cells, neutrophils, monocytes, macrophages and so on.

Human perinatal tissue-derived MSCs are also safe according to numerous clinical trial reports. The safety and initial efficacy of umbilical cord derived MSCs (UC-MSCs) transfusions for acute-on-chronic liver failure (ACLF) patients associated with hepatitis B virus (HBV) infection was assessed. These results suggested that MSCs transfusions are safe in the clinic and may serve as a novel therapeutic approach for HBV-associated ACLF patients [1]. The safety and efficacy of human UC-MSCs in the treatment of rheumatoid arthritis (RA) also was assessed. These results showed that no serious adverse effects were observed during or after infusion. Furthermore, the treatment of MSCs induced a significant remission of disease according to the 28-joint disease activity score [2]. Scientists evaluated the safety and feasibility of intramyocardial MSCs injection in nine patients, shortly after acute myocardial infarction (AMI) during short-term and 5-year follow-up [3]. These results suggested that intramyocardial injection of MSCs in patients shortly after AMI is feasible and safe up to 5-year follow-up. A prospective double blind randomized placebo controlled multi-center study to determine the safety of MSCs in patients with critical limb ischemia showed that MSCs are also safe when injected intramuscularly at a dose of 2 million cells/kg body weight [4]. No neoplastic complications were detected at any MSCs implantation sites. Hongye Fan et al ([15]) showed that the transplantation of IL1β primed MSCs has an enhanced therapeutical efficiency in DSS-induced murine colitis, which depends on their increased immunosuppressive capacities and enhanced migration ability. WO 2014/093948 also disclosed the therapeutic value of purified MSCs.

However, the definition of MSCs has always been controversial because there is no specific or unique cell surface marker identifying them unambiguously. To date, MSCs have been defined by using a combination of cell surface phenotypic protein markers, plastic adherent fibroblast-like growth and functional properties. Yet, there are several different subpopulations according to these cell surface markers and these different subpopulations show different biological characteristics, biological functions and are not all efficient in treatment protocols. For example, some MSC populations are stimulated by IL1β ([12]), whereas other populations are not (the CD106 positive MSCs in [15]). Additionally, the proliferation of some MSC populations is inhibited by IL4 ([12]), whereas other are induced to proliferation in the presence of this cytokine ([13]). There is therefore an urgent need to identify a population of functional MSCs that have a clinical efficiency and standardize their preparation process. It is also important to set up a protocol that can be used on every placental and extra-embryonic tissue interchangeably. More precisely, it is important to identify a preparation process that yields therapeutically efficient MSC populations either from placental tissue or from umbilical cord fragments.

Meanwhile, there is currently a high demand of human MSCs for numerous therapeutic applications but insufficient availability in the market. There is therefore a need for an industrial scale process giving a high yield of functional MSCs. There is also a need for an efficient culturing system that gives an optimum yield at an affordable cost, thereby reducing the demand-supply gap, for MSCs obtained from all placental and extraembryonic tissues.

The present application fulfills all these needs and others, by proposing an optimal method for generating and purifying MSCs subpopulations of different origins (either from placental tissue or from umbilical cord) and ultimately expanding said subpopulation with the least possible passages and minimal number of population doublings. This method leads to the recovery, from placental and from umbilical cord tissues, of highly potent MSCs having a multilineage differentiation capacity. This method reproducibly provides with a considerable number of MSC cells that are suitable for clinical application.

DETAILED DESCRIPTION OF THE INVENTION

Example 1 (see below) discloses a preparation method for generating human placenta tissue derived $CD106^{high}$ $CD151^+$ $Nestin^+$ mesenchymal stem cells (MSCs) at industrial scale, enabling to obtain a yield of at least $1 \times 10^5$ cells/cm$^2$ MSCs which are prepared in a GMP-compliant facility and are suitable for allogenic use. Said placental tissue derived $CD106^{high}$ $CD151^+Nestin^+$ mesenchymal stem cells (MSCs) comprise over 95% of cells which express the positive markers CD73, CD90, CD105 and CD166, and less than 2% of cells which express the negative markers CD45, CD34 and HLA-DR.

This method is useful for generating cells that can be used in transplantation trials into a human subject or in an animal. It comprises the two following general steps:

(i) Culturing mesenchymal stem cells obtained from a biological tissue or fluid in a first culture medium deprived of growth factors, so as to generate a population of cultured undifferentiated mesenchymal stem cells,
and
(ii) contacting said population of cultured undifferentiated mesenchymal stem cells with a second culture medium containing pro-inflammatory growth factors or inflammatory mediators, thereby generating $CD106^{high}$ $CD151^+Nestin^+$ mesenchymal stem cells useful for transplantation into a subject in need thereof.

In a first aspect, the invention relates to an in vitro method to prepare $CD106^{high}$ $CD151^+Nestin^+$ mesenchymal stem cells (MSCs) at industrial scale, said method comprising culturing a population of undifferentiated MSCs in a culture medium comprising pro-inflammatory growth factors or inflammatory mediators.

Said "population of undifferentiated MSCs" can be obtained by collecting the mononuclear cells present in a biological tissue or fluid and growing them in a first culture medium. These mononuclear cells can be obtained by any conventional means, e.g., by enzymatic digestion or explant culture of perinatal tissue pieces [10] or isolation from biological fluids [11].

Explant culture is a particularly preferred process for deriving MSC from umbilical cords, as exposed in example 3 below.

Typically, this process requires to remove the sample from the transport solution, to cut it in sections (roughly 2-3 cm long), to disinfect them with antibiotics and antifungal agents that are rinsed afterwards, to recover the epithelial membrane and dispose pieces of said membrane in flasks for them to adhere (preferably without medium, at room temperature), before complete medium is added carefully on the adhered explants and keep incubated at 37° C. for several days. The migrated cells are eventually collected with appropriate tools and maintained in culture in the appropriate first medium (see below) until they reach the target confluency.

Said "first culture medium" can be any classical medium commonly used to favor growth of living primary cells. Preferably, it does not contain any growth factors nor any differentiation factors.

The skilled person well knows what kind of culture media can be used as "first culture medium". They are for example DMEM, DMEM/F12, MEM, alpha-MEM (α-MEM), IMDM, or RPMI. Preferably, said first culture medium is DMEM (Dulbecco's Modified Eagle's Medium) or DMEM/F12 (Dulbecco's Modified Eagle's Medium: Nutrient Mixture F-12).

More preferably, said first culture medium contains 2-20% or 2-10% of fetal bovine serum. Alternatively, said first culture medium may contain 1-5% platelet lysate. A most preferred medium contains 2-20% or 2-10% of fetal bovine serum and 1-5% platelet lysate.

It is also possible to use as first culture medium a medium which is devoid of serum or platelet lysate, provided that it contains other appropriate agents favoring the growth of primary living cells.

In a preferred embodiment, said "biological tissue" is any portion of a placental tissue, or of umbilical cord. In particular, it can include or consist in placental cotyledons, the amnion membrane or the chorionic membrane of the placenta. Also, it can be the Wharton jelly found in the umbilical cord. It can include the veins and/or the arteries, or be deprived thereof.

In another embodiment, said "biological fluid" is a sample of umbilical cord blood, of placenta blood or of amniotic fluid, which have been harmlessly collected from a woman or a mammal in general. For example, these tissues and fluids can be obtained after the delivery of a baby or an offspring, without any invasive proceedings.

Said population of undifferentiated MSCs is preferentially a population of mesenchymal stem cells seeded on a plastic surface, which has been cultured in said first culture medium devoid of any growth factor until the cells reach a confluency of 85-90%.

Regularly, the cells are phenotypically characterized by FACS or any conventional means, in order to detect the level of the surface markers CD73, CD90, CD105, CD166, CD45, CD34 and HLA-DR.

When 95% of the cells express the positive surface markers CD73, CD90, CD105 and CD166, and less than 2% express the negative surface markers CD45, CD34 and HLA-DR, the cells are trypsinized and seeded again at a lower density, e.g. at a density of 1000 to 5000 MSCs per $cm^2$ into a second culture medium.

Preferably, said "second culture medium" is any classical medium commonly used to favor living primary cells growth. It can be the same medium as the "first culture medium", or it can be another one, chosen for example among DMEM, DMEM/F12, MEM, alpha-MEM (α-MEM), IMDM, or RPMI. More preferably, said second culture medium is DMEM (Dulbecco's Modified Eagle's Medium) or DMEM/F12 (Dulbecco's Modified Eagle's Medium: Nutrient Mixture F-12).

Even more preferably, said second culture medium contains serum or platelet lysate, for example between 2-20% of fetal bovine serum and/or 1-5% platelet lysate. A most preferred second medium is DMEM containing 2-20% of fetal bovine serum and 1-5% platelet lysate. It is also possible to use as second culture medium a medium which is devoid of serum or platelet lysate, provided that it contains other appropriate agents favoring the growth of primary living cells.

When the cells reach 40-50% confluency, pro-inflammatory growth factors or inflammatory mediators are added to the second culture medium and the cells are cultured in said medium until they reach 90-95% confluency.

Said "pro-inflammatory growth factors" are typically interleukins or chemokines that are known to have a pro-inflammatory effect. Examples of interleukins that can be added in the second culture medium include TNFα, IL1, IL4, IL12, IL18, and IFNγ. Examples of chemokines that can be added in the second culture medium include CXCL8, CXCL10, CXCL1, CXCL2, CXCL3, CCL2, and CCL5. Other inflammatory mediators (such as anti-inflammatory agents) can be used.

In a preferred embodiment, at least two pro-inflammatory growth factors are added in the second culture medium defined above. These at least two pro-inflammatory growth factors are chosen in the group consisting of: TNFα, IL1, IL4, IL12, IL18, and IFNγ. In a more preferred embodiment, said pro-inflammatory growth factors are chosen among IL1, IL4, IL12, IL18. Even more preferably, they are IL1 and IL4.

A typical concentration of growth factor(s) that can be added to the MSCs is comprised between 1-200 ng/mL, preferably between 1-100 ng/mL, more preferably between 10-80 ng/mL. Preferably, the culturing step of the MSCs with the growth factor(s) lasts for at least one day, more preferably for two days.

The term "IL1" herein designates any isoform of Interleukin 1, in particular, IL1α and IL1β. IL1 isoforms may be of various origins, depending on the intended application. For example, animal IL1 may be used for veterinary applications. Preferably, only IL1β is added in the second culture medium of the invention. In this particular embodiment, the concentration of added Interleukin 1β can be comprised between 1-100 ng/mL, preferably between 1-50 ng/mL, more preferably between 10-40 ng/mL.

Human IL1 beta (IL1β) is referenced to as accession number NP_000567.1 (SEQ ID NO:6, 269 amino acids). Recombinant protein is commercially available in GMP conditions (RnD systems, Thermofisher, Cellgenix, Peprotech).

The term "IL4" herein designates any isoform of Interleukin 4. IL4 may be of various origins, depending on the intended application. For example, animal IL4 may be used for veterinary applications.

Human IL4 is referenced to as accession number AAA59149 (SEQ ID NO:7, 153 amino acids). Recombinant protein is commercially available in GMP conditions (RnD systems, Thermofisher, Cellgenix, Peprotech).

Any mixture of different pro-inflammatory growth factors can be used in the second medium of the invention. In particular, it is a preferred embodiment to use a mixture of IL1 and IL4, more precisely, of IL1β and IL4, as disclosed in the experimental part below.

In this particular embodiment, the added Interleukin 1β has a concentration comprised between 1-100 ng/mL, preferably between 1-50 ng/mL, more preferably between 10-40 ng/mL. and the added IL4 has a concentration comprised between 1-100 ng/mL, preferably between 1-50 ng/mL, more preferably between 10-40 ng/mL in the second culture medium. Preferably, the culturing step with Interleukin 1β and IL4 lasts for at least one day, more preferably for two days.

In a final step, the cells are phenotypically characterized by any conventional means, in order to detect the level of surface markers CD73, CD90, CD105, CD166, CD45, CD34 and HLA-DR. These markers are well-known in the art. Antibodies useful for detecting the expression level of these markers are all commercially available.

Expression of these cell surface markers may be notably assessed using well known technologies such as cell membrane staining using biotinylation or other equivalent techniques followed by immunoprecipitation with specific antibodies, flow cytometry, western blot, ELISA or ELISPOT, antibodies microarrays, or tissue microarrays coupled to immunohistochemistry. Other suitable techniques include FRET or BRET, single cell microscopic or histochemistry methods using single or multiple excitation wavelength and applying any of the adapted optical methods, such as electrochemical methods (voltametry and amperometry techniques), atomic force microscopy, and radio frequency methods, e.g. multipolar resonance spectroscopy, confocal and non-confocal, detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry), cell ELISA, radioisotopic, magnetic resonance imaging, analysis by polyacrylamide gel electrophoresis (SDS-PAGE); HPLC-Mass Spectroscopy; Liquid Chromatography/Mass Spectrometry/Mass Spectrometry (LC-MS/MS).

Preferably, the levels of cell surface markers are assessed by FACS. In other words, the method of the invention typically requires to:

a) collect the mononuclear cells contained in a perinatal biological tissue or fluid, b) allow said mononuclear cells to grow into a first culture medium until they reach 85-90% confluence, preferably on a plastic surface, c) once 95% of the cells express the positive markers CD73, CD90, CD105 and CD166, and less than 2% express the negative markers CD45, CD34 and HLA-DR, seed the cells at a density of 1000 to 5000 MSCs per cm$^2$ into a second culture medium, d) add between 1-100 ng/mL of inflammatory mediators or pro-inflammatory growth factors once the cells reach 40-50% confluency, e) collect the cells when they reach 90-95% confluency.

The collected cells may then be phenotypically characterized by FACS or any conventional means, in order to detect the level of surface markers CD73, CD90, CD105, CD166, CD45, CD34 and HLA-DR. Said first and second culture media have been described above.

In step d) of said method, the typical concentration of added growth factor(s) is comprised between 1-200 ng/mL, preferably between 1-100 ng/mL, more preferably between 10-80 ng/mL. Preferably, the culturing step with growth factor(s) lasts for at least one day, more preferably for two days.

In a particular embodiment of the invention, the concentration of added Interleukin 1β or IL4 can be comprised between 1-100 ng/mL, preferably between 1-50 ng/mL, more preferably between 10-40 ng/mL. Preferably, the culturing step with Interleukin 1β, and IL4 lasts for at least one day, more preferably for two days.

The final collected cells will be the "cell culture of the invention", or "CD106$^{high}$ CD151$^+$Nestin$^+$ MSCs of the invention" or "MSCs of the invention". This cell culture typically comprises over 60%, preferably between 60 and 70%, preferably over 70%, preferably over 80%, more preferably over 90% and even more preferably over 95% of cells expressing CD106. Moreover, it comprises over 98%, preferably over 99% of cells expressing CD151. Moreover, it comprises over 98%, preferably over 99% of cells expressing Nestin, Finally, it comprises over 95%, preferably over 96%, preferably over 97%, preferably over 98% of cells expressing the positive markers CD73, CD90, CD105 and CD166, and comprises less than 2% cells expressing the negative markers CD45, CD34 and HLA-DR.

CD106 (also known as VCAM-1 for "vascular cell adhesion protein 1") is known to have three isoforms. NP_001069.1 (herein referred to as SEQ ID NO:1, 739 amino acids), NP_542413.1 (herein referred to as SEQ ID NO:2, 647 amino acids) and NP_001186763.1 (herein referred to as SEQ ID NO:3, 677 amino acids) are the sequences of the isoforms a, b and c respectively. Antibodies to detect the level of expression of this particular biomarker are commercially available (for example by Thermofisher, Abcam, OriGen, etc.). The expression of this marker at the surface of the cells of the invention is very important, as it triggers pro-angiogenic activities that are essential for their therapeutic use.

The nestin biomarker (herein referred to as SEQ ID NO:4, 1621 amino acids) is referenced under the number NP_006608.1 in humans. Antibodies to detect the level of expression of this particular biomarker are commercially available (for example by Thermofisher, Abcam, etc.).

The CD151 biomarker (herein referred to as SEQ ID NO5, 253 amino acids) is referenced under the number NP_620599 in humans. Antibodies to detect the level of expression of this particular biomarker are commercially available (for example by Invitrogen, Sigma-Aldrich, Abcam, etc.).

In a preferred embodiment, the culturing steps (or growing steps) are performed on a plastic surface.

More specifically, the method of the invention may comprise the steps of:

a) Optionally separately collecting placental tissues from multiple donors;
b) Optionally washing the placental tissue three times using 1×PBS, dissected in 1 mm³ cubes and washing the cubes tissue again to remove most of the blood from the tissue.
c) Optionally digesting the placental tissue of each donor separately with collagenase, centrifuging the digested tissue and collecting the mononuclear cells,
d) Seeding the collected mononuclear cells into a culture medium;
e) Trypsinizing and passage the cells once they reach 85-90% confluence;
f) Characterizing the cells based on the percentage of cells which express positive markers CD73, CD90, CD105 and CD166, and negative markers CD45, CD34 and HLA-DR;
g) Seeding the cells in a culture medium containing 90% Dulbecco's Modified Eagle's Medium/F12-Knockout (DMEM/F12-KO) and 10% FBS and growth factors at a seeding density of 1000 to 5000 MSCs per cm² when they comprise at least 95% of the positive markers and at most 2% of the negative markers,
h) Adding between 1-100 ng/mL of interleukin 1β and optionally between 1-100 ng/mL of IL4 when they are 40-50% confluent;
i) Trypsinizing and collecting the cells once they reach 90-95% confluence; and
j) Optionally characterizing the cells based on the percentage of cells which express positive markers CD73, CD90, CD105 and CD166, and negative markers CD45, CD34 and HLA-DR. The results disclosed below show that the expression of CD106 is greatly enhanced at the surface of the MSCs obtained by the method of the invention either from umbilical cord or placenta. This expression is of high importance for the therapeutic use of the thus generated cells (see below).

The present application therefore also relates to a method to enhance the CD106 expression level of undifferentiated MSCs, said method comprising culturing a population of undifferentiated MSCs in the particular conditions exposed thoroughly above, all the detailed embodiments applying mutatis mutandis.

In another aspect, the invention relates to a cell culture obtained by the above-described method. This cell culture typically contains isolated CD106$^{high}$ CD151$^+$Nestin$^+$ MSCs expressing the vascular cell adhesion molecule 1 (VCAM-1) marker at a detectably higher level than mesenchymal stem cells derived from adult bone marrow, adipose tissue, umbilical cord or placenta that have not been in contact with any growth factors during their preparation.

In a preferred embodiment, the cell culture of the invention is characterized in that:

(i) over 60%, preferably over 70%, more preferably over 80% and even more preferably over 90% of cells express CD106 at a detectable level, and
(ii) over 98%, preferably over 99% of cells express CD151 at a detectable level, and
(iii) over 90%, preferably over 92%, more preferably over 95% of cells express Nestin at a detectable level, and
(iv) over 95%, preferably over 96%, preferably over 97%, preferably over 98% of cells expressing the positive markers CD73, CD90, CD105 and CD166 at a detectable level.

In a more preferred embodiment, the said cell culture is characterized in that it contains over 98% of MSCs that do not express the markers CD11 b, CD14, CD15, CD16, CD31, CD34, CD45, CD49f, CD102, CD104 and CD133 at a detectable level. These markers are well-known in the art and antibodies detecting same are commercially available.

In a preferred embodiment, the cell culture of the invention contains:

over 60%, preferably over 70%, more preferably over 80% and even more preferably over 90% of cells expressing CD106 at a detectable level, and over 98%, preferably over 99% of cells expressing CD151 at a detectable level, and over 98%, preferably over 99% of cells expressing Nestin at a detectable level, and over 95%, preferably over 96%, preferably over 97%, preferably over 98% of cells expressing the markers CD73, CD90, CD 105 and CD 166 at a detectable level, and less than 2% of cells which express the markers CD45, CD34 and HLA-DR at a detectable level.

According to the present invention, a cell "expresses a marker at a detectable level" if said marker is present at a significant level on its surface, i.e., if the signal associated to the staining of said surface marker (typically obtained with an antibody recognizing said marker, said antibody being for example coupled to a fluorescent dye) which is measured for said cell is superior to the signal corresponding to the staining of one cell being known as not expressing said marker. The skilled person is well aware of how to identify said cells/markers so that these protocols do not need to be detailed here.

The results disclosed in the experimental part of the present application show that the cell culture obtained by the method of the invention is capable of inducing angiogenesis in vitro and in vivo. These results moreover show that administering said cells to individuals (human or animal subjects) suffering from an ischemic disease or from a disorder of the circulatory system results in a detectable improvement of one or more symptoms of said disease or disorder.

The results disclosed below also show that the methods of the invention enable to generate cells expressing high level of the CD106/VCAM1 membrane protein. Importantly, this protein has been recently associated to the expression of pro-angiogenic cytokines. Therefore, CD106+ MSCs have been selected for their pro-angiogenic efficiency, and proposed as a treatment for hindlimb ischemia ([16], [17]).

Therefore, in a third aspect, invention relates to the use of said cells as a medicament for treating an individual suffering from an ischemic disease or from a disorder of the circulatory system. In other words, the invention relates to the use of said cells for the manufacture of a medicament intended to be used for treating subjects suffering from an ischemic disease or from a disorder of the circulatory system. The medicament of the invention can also be applied to skin vascular capillary network and may include dermatological and cosmetic applications.

Any mammal may be treated by the cells of the invention. Said mammal can be a pet (a dog, a cat, a horse, etc.) or a cattle animal (a sheep, a goat, a cow, etc.). It is obvious for the skilled person that, when an animal is to be treated according to the method of the invention, the initial undifferentiated MSCs will be obtained from a biological sample from the same animal species (allogenic graft) or from a similar species (heterologous graft), and the growth factors that are used in the second culture medium will correspond to those of the same animal species. For example, if a cat is to be treated, then the initial MSCs will be obtained from a perinatal tissue or biological fluid of a cat, and a cat IL1β (recombinant or not) will be added in the second culture medium, optionally along with cat IL4.

In a preferred embodiment, said mammal is a human being. In this case, the initial MSCs will be obtained from a perinatal tissue or from a biological fluid obtained from a woman, and human IL1β (recombinant or not, e.g., SEQ ID NO:6) will be added to the second culture medium, optionally along with human IL4 (e.g., of SEQ ID NO:7).

In this aim, the cell culture of the invention may be transplanted or topically applied to said subject by any conventional means. In this case, the present invention is drawn to a method for treating a subject suffering from an ischemic disease, a disorder of the circulatory system, an immune disease, an organ injury or an organ function failure, said method comprising the step of transplanting the cell culture described above to said subject. This transplantation may be performed by using an implanted reservoir or by injecting the cells in situ in the muscle, or via intravenous injections or by any appropriate delivery system. The application may also be performed topically, by directly contacting the cells with skin or a mucous membrane, or by applying the cells with a device on the skin or on any mucous membrane, or by delivering the cells by any appropriate delivery system to the skin or mucous membrane.

Preferably, said disease or disorder is chosen in the group consisting of: type-1 diabetes mellitus, type-II diabetes, GVHD, aplastic anemia, multiple sclerosis, Duchenne muscular dystrophy, rheumatoid arthritis, cerebral stroke, idiopathic pulmonary fibrosis, dilated cardiomyopathy, osteoarthritis, cirrhosis, liver failure, kidney failure, peripheral arterial occlusive disease, critical limb ischemia, peripheral vascular disease, heart failure, diabetic ulcer or any degenerative disease, synechia, endometrial disorder or fibrotic disorder of the gastro-intestinal tract such as anal fistula. More preferably, said disease or disorder is a peripheral arterial occlusive disease, a critical limb ischemia, a peripheral vascular disease, or a diabetic ulcer. In a particular embodiment, said disease or disorder is a skin or a mucous membrane disease, including (but not limited to) a diabetic ulcer, an ulcer, a trauma, a burn, a scald, a wound or a wound healing problem, Decubitus ulcer, a wart, etc.

The cell culture of the invention may more precisely be used in a dermatological preparation whose aim is to treat skin pathologies such as burns, wounds, ulcers, scars, warts, or other diseases such as synechia or fibrotic disorders of the gastro-intestinal tract (for example anal fistula).

In another particular embodiment, said disease or disorder is anal fistula or endometrial injury.

Other applications are encompassed within the present application. In particular, it is possible to use the MSCs of the invention for dermatologic or cosmetic purposes, for example for regenerating the cells of the skin or of a mucosal membrane, improving the aspect of the skin or of a mucosal membrane, correcting a defect of the skin or of a mucosal membrane or for healing burning area of the skin or of the mucosal membrane.

In order to enhance the efficiency and facilitate the administration of the medicament of the invention, the cell culture of the invention may be mixed with any agent, composition of agents or other biologically compatible material or device. The cell culture of the invention may also be encapsulated or included in any appropriate delivery system or biocompatible material. The cells or preparation containing the cells may be applied with a medical device, such as a endoscope, a stent, or a syringe, for example. It can be also applied topically by contacting the cells with the skin or a mucosa.

The present invention also targets a medical device containing the cell culture of the invention. By "medical device", it is herein encompassed any instrument, apparatus, implement, machine, appliance, implant, reagent for administering a therapeutic composition. In the context of the invention, said medical device is, for example, a patch, a stent, an endoscope, or a syringe.

The present invention also targets a delivery system containing the cell culture of the invention. By "delivery system", it is herein encompassed any system (medium or carrier) for administering a pharmaceutical product to a patient. It can be an oral delivery or a controlled-release system. In the context of the invention, said delivery system is for example liposomes, proliposomes, microspheres, micro- or nano-vesicles of biopolymers, lipids or nanoparticles.

In a preferred embodiment of the invention, the cells of the invention are included in an hydrogel or another biocompatible material or excipient. Said hydrogel may include notably alginate sodium hydrogel, hyaluronic acid hydrogel, chitosan hydrogel, collagen hydrogel, HPMC Hydrogel, Poly-L-lysine hydrogel, Poly-L-glutamic acid hydrogel, polyvinyl alcohol (PVA) hydrogel, polyacrylic acid hydrogel, polymethylacrylic acid hydrogel, polyacrylamide (PAM) hydrogel, and Poly N acrylamide (PNAM) hydrogel.

The present invention also relates to a hydrogel containing the MSCs of the invention and possibly another biocompatible material or excipient. An alginate hydrogel is herein preferred, such as for the alginate hydrogel described in CN106538515.

In the context of the present invention, "biocompatible materials" are those classically used in biomedical applications. They are for example metals (such as stainless steel, cobalt alloys, titanium alloys), ceramics (aluminium oxide, zirconia, calcium phosphates), polymers (silicones, poly (ethylene), poly(vinyl chloride), polyurethanes, polylactides) or natural polymers (alginate, collagen, gelatin, elastin, etc.). These materials may be synthetic or natural. Biocompatible excipients are well-known in the art and do therefore not need to be detailed.

This hydrogel can be used for cosmetic or therapeutic purposes.

The present invention also concerns a pharmaceutical or a veterinary composition containing the cell culture of the invention, as well as its use for treating the diseases and disorders mentioned above. It also concerns a dermatologic or cosmetic composition containing the cell culture of the invention.

This pharmaceutical, veterinary or cosmetic composition may further contain other biocompatible agents (e.g., an hydrogel) as described above.

Said composition preferably contains at least about 1 to $5 \times 10^6$ cells.

DESCRIPTION OF THE FIGURES

In order that the disclosure may be readily understood and put into practical effect, reference will now be made to exemplary embodiments and illustrated figures. The figures together with a detailed description below serve to further illustrate the embodiments and explain various principles and advantages in accordance with the present disclosure.

EXAMPLES

For simplicity and illustrative purposes, the present invention is described by referring to exemplary embodiments thereof. It will be apparent, however, to one of ordinary skill in the art that the present invention may be practiced without limitation to these specific details. In other instances, well known methods have not been described in detail so as not to unnecessarily obscure the present invention.

1. Method to Obtain the MSCs of the Invention from Placental Tissue

The method of the invention has been realized by:
a) separately collecting human placenta tissue from multiple mother donors;
b) washing the placenta tissue three times using 1×PBS, dissected in 1 $mm^3$ cubes and washing the cubes tissue again to remove most of the blood from the tissue.
c) digesting the placenta tissue of each donor separately with collagenase, centrifuging the digested tissue and collecting the mononuclear cells,
d) seeding the mononuclear cells into a culture medium;
e) trypsinizing and passage the cells once they reach 85-90% confluence;
f) characterizing the cells based on the percentage of cells which express positive markers CD73, CD90, CD105 and CD166, and negative markers CD45, CD34 and HLA-DR;
g) seeding the cells in a culture medium containing 90% Dulbecco's Modified Eagle's Medium/F12-Knockout (DMEM/F12-KO) and 10% FBS and growth factors at a seeding density of 1000 to 5000 MSCs per $cm^2$ when they comprise at least 95% of the positive markers and at most 2% of the negative markers,
h) obtaining $CD106^{high}$ $CD151^+Nestin^+$ MSCs comprising over 80% cells which express CD106, 98% for CD151, 98% for Nestin, and 95% cells which express positive markers CD73, CD90, CD 105 and CD 166, and less than 2% cells which express negative markers CD45, CD34 and HLA-DR (for transplantation use) and adding 20 ng/mL of IL1β (provided by Peprotech) and 20 ng/mL of IL4 (provided by Peprotech) when they are 40-50% confluent;
i) trypsinizing and collecting the cells once they reach 90-95% confluence;
j) characterizing the cells based on the percentage of cells which express positive markers CD73, CD90, CD105 and CD166, and negative markers CD45, CD34 and HLA-DR.

This method enabled to generate a subpopulation of placental-derived MSCs with a yield of at least $1×10^5$ cells/$cm^2$ MSCs ($5×10^6$ MSCs in T75 $cm^2$ flasks when they are 90% confluent) that can be used in allogenic administrations. These cell cultures comprised over 95% cells which express positive markers CD73, CD90, CD105 and CD166, and less than 2% cells which express negative markers CD45, CD34 and HLA-DR.

Figure 2:
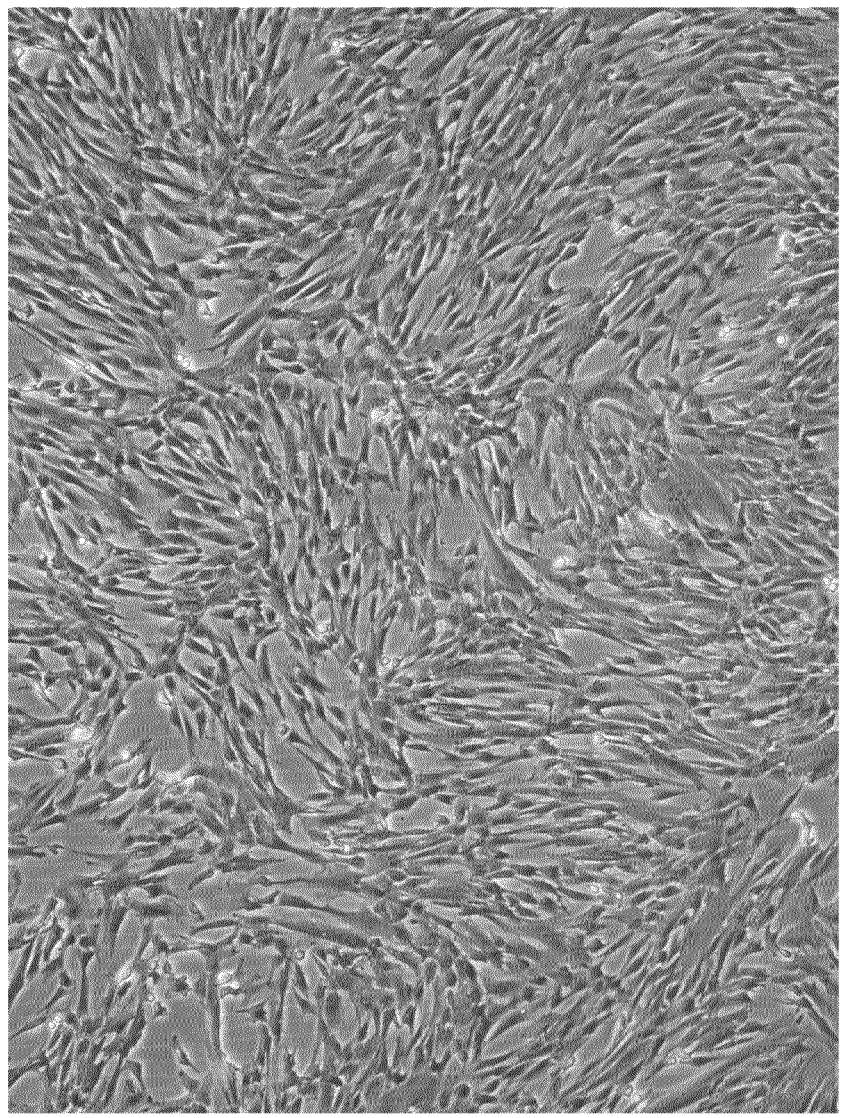
FIG. 2 shows the morphology of the MSCs attached to culture flasks in placenta, according to Example 1.
Figure 3:
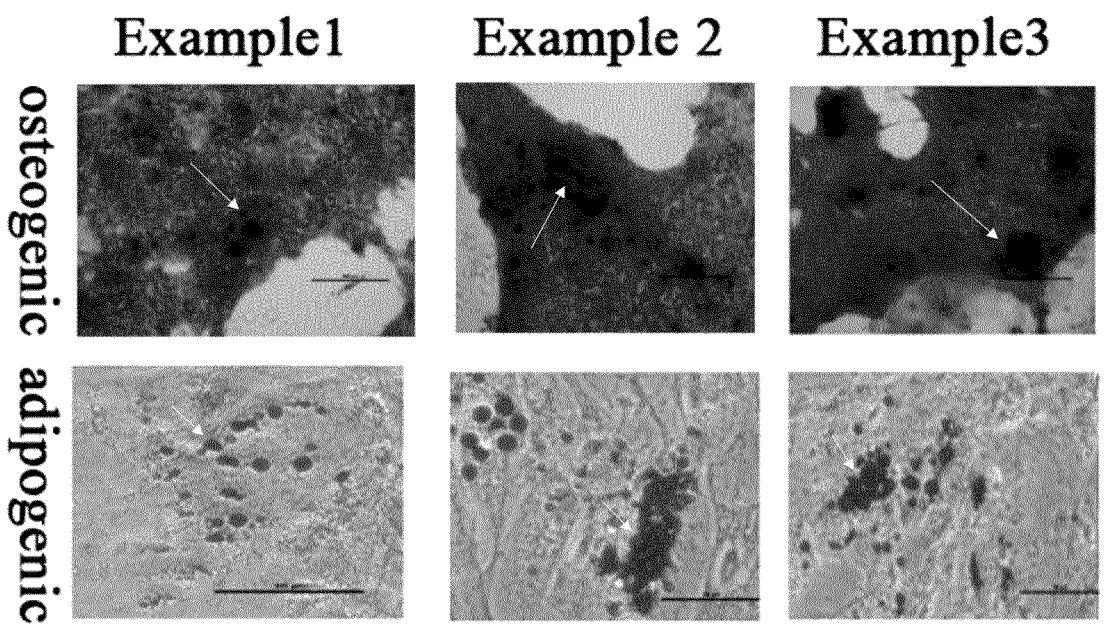
FIG. 3 shows the adipogenic and osteogenic cell differentiation of $CD106^{high}$ $CD151^+Nestin^+$ MSCs. The results show that $CD106^{high}$ $CD151^+Nestin^+$ MSCs subpopulation are capable of adipogenic and osteogenic differentiation in appropriate medium. The white arrows highlight lipid droplets and strongly mineralized area.

The human perinatal tissue derived $CD106^{high}$ $CD151^+Nestin^+$ MSCs were fibroblast-like and grow very well on plastic flask (cf. FIG. 2).

Figure 1:
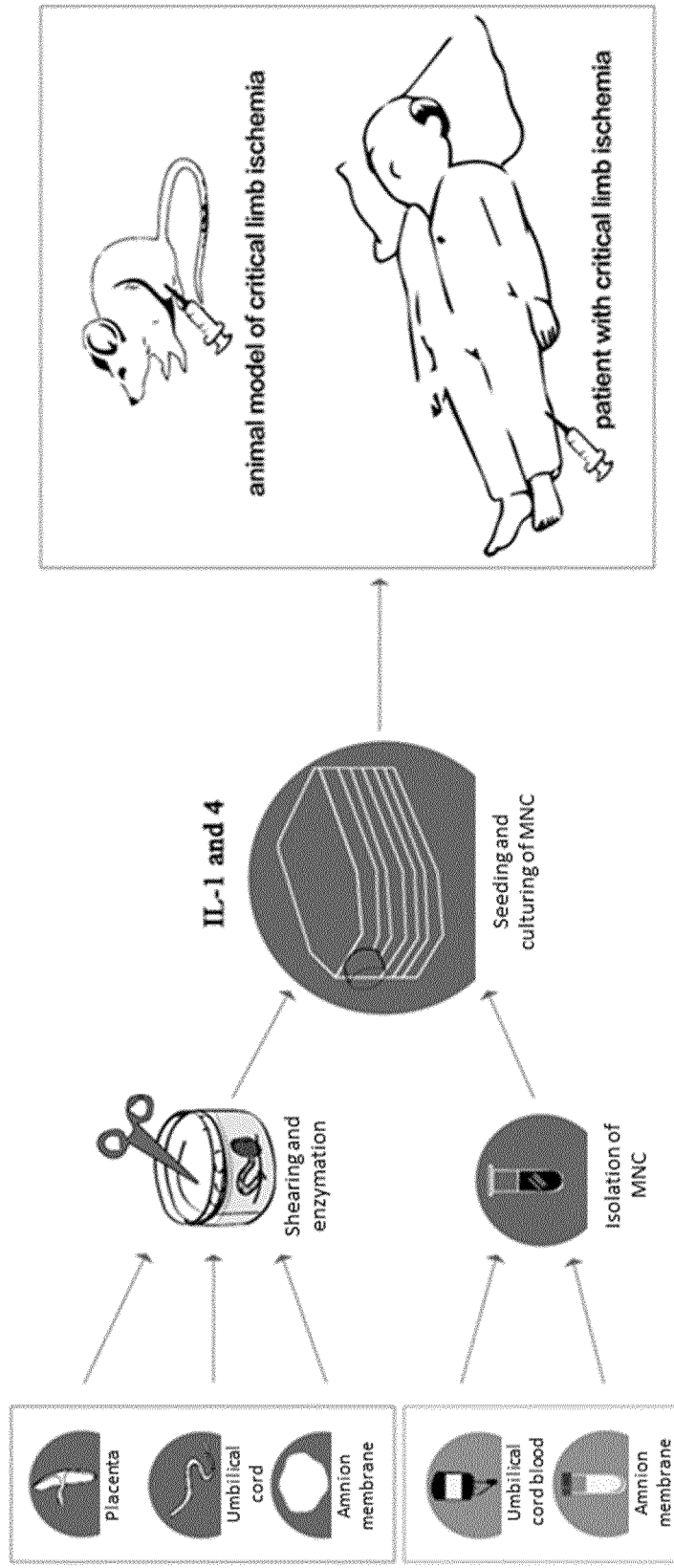
FIG. 1 discloses a diagram showing how the $CD106^{high}$ $CD151^+Nestin^+$ MSCs subpopulation of the invention can be prepared.

Three independent experiments have been performed (experiment 1, experiment 2 and experiment 3). 20 ng/mL of both Interleukin 1 (β) and 4 have been added when the cells are 40-50% confluent (see FIG. 1). At that point, MSCs comprise over 95% cells which express the positive markers CD73, CD90, CD105 and CD166, and less than 2% cells which express the negative markers CD45, CD34 and HLA-DR. After this, MSCs keep growing till 90% cell confluent (see Tables 1 and 2 below), in practice during about 2 days.

Of note, the expression of MSCs cell surface protein CD106, CD151 and Nestin increased significantly after the interleukin 1 and 4 were added.

TABLE 1 shows the expression of CD11b, CD19, CD29, CD31, CD34, CD45, CD73, CD90, CD 105, CD106, CD151, Nestin and HLA-DR on placenta tissue derived MSCs before adding interleukin 1 and 4 obtained in placenta Example 1, 2, and 3. These results show that placenta derived MSCs have classical cellular surface markers just like bone marrow and adipose tissue derived MSCs.

TABLE 1

| Surface markers | Experiment 1 | Experiment 2 | Experiment 3 |
|---|---|---|---|
| IgG-PE | 0.4% | 0.9% | 0.1% |
| IgG-FITC | 0.5% | 0.1% | 0.4% |
| CD11b-PE | 0.2% | 1.4% | 0.3% |
| CD19-FITC | 0.7% | 0.2% | 0.6% |
| CD34-FITC | 0.9% | 0.1% | 0.3% |
| CD45-PE | 0.2% | 1.1% | 0.3% |
| CD31-FITC | 0.3% | 0.1% | 0.4% |
| CD73-PE | 99.2% | 99.1% | 99.8% |
| CD90-PE | 99.7% | 100% | 98.9% |
| CD105-FITC | 96.7% | 98.1% | 98.8% |
| CD106-PE | 31.5% | 23.2% | 30.6% |
| CD151-PE | 95.6% | 96.1% | 93.8% |
| CD29-PE | 99.4% | 100% | 99.9% |
| CD44-FITC | 99.6% | 99.4% | 99.2% |
| Nestin-PE | 82.5% | 78.7% | 84.1% |
| HLA-DR-PE | 0.0% | 0.9% | 0.0% |

TABLE 2 shows the expression of CD11b, CD19, CD29, CD31, CD34, CD45, CD73, CD90, CD 105, CD106, CD151, Nestin and HLA-DR on the placenta tissue derived MSCs after adding interleukin 1 and 4 in Experiments 1, 2 and 3. The results show that CD106 and Nestin protein marker increased significantly 48 hours after adding the IL-1 and IL-4 in complete medium. Meanwhile, the CD106$^{high}$ CD151$^+$Nestin$^+$ cells still have classical MSCs cellular surface phenotypic marker.

TABLE 2

| Surface markers | Experiment 1 | Experiment 2 | Experiment 3 |
|---|---|---|---|
| IgG-PE | 0.1% | 0.6% | 0.2% |
| IgG-FITC | 0.2% | 0.4% | 0.4% |
| CD11b-PE | 0.2% | 1.0% | 0.1% |
| CD19-FITC | 0.4% | 0.8% | 0.8% |
| CD34-FITC | 0.4% | 0.2% | 0.5% |
| CD45-PE | 0.5% | 0.8% | 0.7% |
| CD31-FITC | 0.7% | 0.5% | 0.8% |
| CD73-PE | 99.9% | 99.9% | 99.7% |
| CD90-PE | 99.3% | 100% | 99.7% |
| CD105-FITC | 99.8% | 99.8% | 95.5% |
| CD106-PE | 82.7% | 81.9% | 84.3% |
| CD151-PE | 98.2% | 99.4% | 98.3% |
| CD29-PE | 100% | 100% | 99.6% |
| CD44-FITC | 99.8% | 99.8% | 99.6% |
| Nestin-PE | 93.7% | 92.9% | 90.6% |
| HLA-DR-PE | 0.0% | 1.3% | 0.5% |

These subpopulations can secrete more cellular growth factors, cytokines, immunomodulation factors and inflammation factors (see Table 3). These CD106$^{high}$ CD151$^+$ Nestin$^+$ MSCs will therefore have a better potential of immunomodulation and angiogenesis.

Table 3 shows the related expression levels of growth factors secreted in the spent media by q-PCR. The results show that placenta tissue derived MSCs have more protein expression or secretion of IL-6, IL-8, IL-10, HGF, ANG, MMP2, VEGF-A and TGF-β at 48 hours after adding IL-1 and IL-4 in complete medium.

TABLE 3

| Growth factors | Before IL-1 and il-4 | Post IL-1 and IL-4 | T-test |
|---|---|---|---|
| IL-6 | 1.03 ± 0.29 | 15.06 ± 3.24 | P < 0.05 |
| IL-8 | 1.07 ± 0.31 | 13.74 ± 4.51 | P < 0.05 |
| IL-10 | 0.82 ± 0.31 | 7.84 ± 2.32 | P < 0.05 |
| HGF | 0.85 ± 0.42 | 4.19 ± 1.63 | P < 0.05 |
| ANG | 1.13 ± 0.28 | 3.58 ± 1.25 | P < 0.05 |
| MMP 2 | 0.95 ± 0.42 | 3.92 ± 1.29 | P < 0.05 |
| VEGF-A | 1.18 ± 0.24 | 2.83 ± 0.76 | P < 0.05 |
| TGF-β | 0.96 ± 0.29 | 2.07 ± 0.37 | P < 0.05 |
| bFGF | 1.05 ± 0.35 | 1.47 ± 0.44 | P > 0.05 |
| SDF | 1.13 ± 0.27 | 1.92 ± 0.66 | P > 0.05 |

2. Method to Obtain the MSCs of the Invention from Umbilical Cord Tissues

The following reagents have been used in the present example:

| | | |
|---|---|---|
| Cellgenix | 001011-050 | IL-1b GMP |
| Cellgenix | 001003-050 | IL-4 GMP (250 µg/mL) Aliquots 15 µL |
| Peprotech | 200-01B | Recombinant Human IL-1b 100 µg |
| Peprotech | 200-04 | Recombinant Human IL-4 100 µg |
| BD | 555749 | PE Mouse IgG1, Isotype Control |
| BD | 555647 | PE Mouse Anti-Human CD106 51-10C9 RUO |
| BD | 550257 | PE Mouse Anti-Human CD73 AD2 RUO |
| BD | 556057 | PE Mouse Anti-Human CD151 14A2.H1 RUO |
| Miltenyi | 130-081-002 | CD34-PE, human |
| Miltenyi | 130-092-654 | CD31-FITC, human |
| Miltenyi | 130-099-295 | CD90-PE-Vio770, human |
| Miltenyi | 130-111-788 | Anti-HLA-DR-FITC, human |
| Miltenyi | 130-094-941 | CD105-PE, human |
| Miltenyi | 130-110-631 | CD45-FITC, human |
| Miltenyi | 130-091-835 | Mouse IgG2a-PE |
| Miltenyi | 130-092-213 | Mouse IgG1-FITC |
| Miltenyi | 130-096-654 | Mouse IgG1-PE-Vio770 |
| Miltenyi | 130-104-693 | MACS Comp Bead Kit anti-REA |
| Miltenyi | 130-097-900 | MACS Comp Bead Kit anti-Mouse Igk |

2.1. Cell Isolation by Explant Method

The umbilical cord was removed from the transport solution and cut in 2-3 cm long sections. To avoid contamination by adherent blood cells, each cord segment containing a blood clot that cannot be removed was discarded. The sections were then disinfected in a bath of antibiotics and antifungal agents composed of αMEM+Vancomycin 1 g/L+ Amoxicillin 1 g/L+Amikacin 500 mg/L+Amphotericin B 50 mg/L for 30 min at room temperature (RT). Antibiotics were extemporaneously dissolved in sterile water for injection.

The sections of umbilical cord were removed from the bath and quickly rinsed in 1×PBS at RT. The epithelial membrane was slightly sectioned without touching the vessels. Each section was then detailed in slices of 0.5 cm thickness and disposed at the bottom of a 150 cm² plastic flask with lid. 6 to 10 slices per flask were disposed with at least a 1 cm radius circle of free space around each slice, and left to adhere for 15 min without medium at RT.

After adhesion, complete medium (αMEM+5% CPL+2 U/mL heparin) was added carefully, to keep the explants adherent to the bottom of the flask. The flasks were then incubated at 37° C., 90% humidity and 5% CO2.

The culture medium was changed after 5 to 7 days.

At day 10 after isolation, the migration of the cells out of the explants was controlled by inverted microscopy. If a circle of adherent cells was visible around most of the explants, they were carefully removed, by picking them out of the flask, through the lid, with a sterile, disposable, single-use pair of tweezers.

From this step, the confluency of the cells was visually checked every other day and, if needed, a medium change was performed at day 17.

When the cells reached 70-90% confluency or at D20, the medium was removed and cells were washed with 30 mL of 1×PBS per flask. Cells were then removed with Trypzean® and collected with the old medium and centrifuged 10 min at 2500 rpm. Supernatant was discarded and cells were then suspended in a cryopreservation solution consisting in αMEM+100 mg/mL HSA+10% DMSO and cryopreserved.

2.2. Cell Isolation by Enzymatic Method

The umbilical cord was removed from the transport solution and cut in 2-3 cm long sections. To avoid contamination by adherent blood cells, each segment containing a blood clot that cannot be removed was discarded. The sections were then disinfected in a bath of antibiotics and antifungal agents composed of αDMEM+Vancomycin 1 g/L+Amoxicillin 1 g/L+Amikacin 500 mg/L+Amphotericin B 50 mg/L for 30 min at room temperature (RD. Antibiotics were extemporaneously dissolved in sterile water for injection.

The cord was then cut in small pieces and immersed in an enzymatic cocktail comprising 2.7 mg/mL collagenase type I and 0.7 mg/mL hyaluronidase, incubated for 3 h at 37° C. with gentle agitation, followed by the addition of 2.5% trypsin and a further incubation for 30 min.

The digested suspension was diluted 1:2 with medium to reduce the viscosity of the suspension and passed through a nylon mesh to obtain single suspension. Cells were centrifuged at 300×g for 20 min, and seeded at 10,000 cells/cm² with fresh medium.

The culture medium was changed after 5 to 7 days and every 7 days after that.

When the cells reached 70-90% confluency or at D20, the medium was removed and cells were washed with 30 mL of 1×PBS per flask. Cells were then removed with Trypzean® and collected with the old medium and centrifuged 10 min at 2500 rpm. Supernatant was discarded and cells were then suspended in a cryopreservation solution consisting in αMEM+100 mg/mL HSA+10% DMSO and cryopreserved.

2.3. Cell Thawing and Culture

Cells were thawed following a classical protocol. Briefly, cryotubes were removed for liquid nitrogen and quickly plunge into a 37° C. water bath. As soon as there was no ice left in the tube, cells were diluted in preheated (37° C.) complete medium (αMEM+0.5% (v/v) ciprofloxacine+2 U/mL heparin+5% (v/v) LP) and quickly centrifuged (300 g, RT, 5 min).

After centrifugation, the cells were suspended in preheated complete medium, and assessed for number and viability (blue trypan/Mallassez hemocytometer).

The cells were seeded in two 75 cm² plastic culture flasks in complete medium, and incubated (90% humidity, 5% $CO_2$, 37° C.).

2.4. Cell Stimulation

After a few days of expansion, the cells were checked for confluency. When confluency reached 30 to 50%, the old medium was discarded and replaced either by fresh complete medium for unstimulated condition, or by fresh medium completed with 10 ng/mL of IL-1β and 10 ng/mL of IL-4.

Cells were then incubated at least 2 days before the flow cytometry experiments.

2.5. Cell Harvesting and Flow Cytometry Analysis

After 2 to 3 days of expansion/stimulation, the cells were checked for confluency. If confluency was up to 80%, the cells were harvested. Briefly, the old medium was discarded and the cells were washed with 1×DPBS. Trypsin EDTA was added and the cells were incubated 5 min at 37° C. Trypsin was neutralized with at least 2× the volume of medium, and the cell suspension was harvested and assessed for number and viability.

The flow cytometry experiment required 1×10⁶ cells, which were centrifuged and resuspended in 1×DPBS+0.4% HSA.

The cells were labelled for CD73, CD90 CD105, CD106, CD151 and CD31, CD34, CD45, HLA-DR according to the following protocol:
1. The cells were assessed for viability and number.
2. The volume of suspension necessary to obtain 20 000 cells/labelling tube was placed in a 15 mL propylene plastic tube.
3. The tube was centrifuged 5 min at 300 g and 4° C.
4. The cells were resuspended with 1×DPBS+0.4% HSA (dilute 10× 4 mg/mL HSA in 1×DPBS). The volume necessary was 500 μL per labelling tube.

Extracellular staining was performed for CD106 and CD151 markers as recommended by the FACS manufacturer and antibodies providers. Intracellular staining was performed for Nestin. For intracellular staining, the Fixation/Permeabilization solution called "BD Cytofix/Cytoperm kit" was used.

If the cells were not analyzed immediately after the staining, a fixation step was performed, by contacting the cells with a 1×DPBS 0.5% formaldehyde solution.

After labelling, the cells were washed with 1×DPBS+ 0.4% HSA and permeabilized for Nestin labelling.

The labelled cells were analyzed with the Accuri C6+ BD Biosciences cytometer, and results were analyzed with the BD Accuri C6 Plus software.

2.6. Results

Several batches of umbilical cord-derived MSCs (HB-COR001 to COR005-MSC) have been obtained by cultivating cord-MSCs isolated by means of the explant methods disclosed above (2.1.) in the conditions exposed in point 2.4. above. For Cord 3 and 5 (COR003 and COR005), two MSC populations (MSC1 and MSC2) have been obtained concomitantly, by repeating the steps of the invention in a separate manner.

The expression of CD106 at the surface of said cells was measured by flow cytometry.

All tested batches of MSC exhibited a drastic increase (>60%) in the CD106 expression levels (see table 4).

TABLE 4

CD106 expression of Umbilical Cord-derived MSCs after stimulation with IL1β and IL4
CD106 levels before and after full stimulation (10 ng/mL of BOTH IL-1b and IL-4)

| Cord Umbilical Cord-derived MSC | % of CD106 before stimulation | % of CD106 after stimulation |
|---|---|---|
| HB1-COR001-MSC1 | 15.71% | 97.34% |
| HB1-COR002-MSC1 | 9.58% | 70.62% |
| HB1-COR003-MSC1 | 8.25% | 69.42% |
| HB1-COR003-MSC2 | 8.25% | 59.47% |
| HB1-COR005-MSC1 | 9.89% | 71.26% |
| HB1-COR005-MSC2 | 9.89% | 75.48% |

3. Impact of the Isolation Protocol on CD106 Expression of Umbilical Cord-Derived MSCs Mesenchymal stem cells were isolated from umbilical cord using the two different methods exposed above (see 2.1. and 2.2.): by explant isolation and by enzymatic digestion.

All cells were cultivated in the same culture medium (αMEM+5% platelet lysate (LP)), stimulated at passage 3 according to the method of the invention and collected 2 days after stimulation. Cells viability is measured and cells were counted.

The expression of several phenotypic markers, including CD106, was then measured by flow cytometry.

All MSCs, whatever the isolation method or the stimulation condition, expressed phenotypic markers in a classical way: CD73, CD90, CD105 are over 95% positive, while CD31, CD34, CD45 and HLA-DR were negative.

CD151+ and Nestin were also both over 95% positive, independently of the stimulation or the isolation method.

Without stimulation, the MSCs isolated by enzymatic digestion expressed higher levels of CD106 before stimulation (53%) than the MSCs isolated with the explants methods (20%) They were however less sensitive to stimulation with the inflammatory cocktail: a smaller increase in CD106 has been observed (+4% increase vs +60% increase).

The explants method is therefore the preferred method of the invention for umbilical cord-derived MSCs.

TABLE 5 viability and cell count of the MSCs obtained after the two experimental protocols exposed in 2.1. and 2.2.

| Condition | COR27Enz P3 + 1 MSCs isolated by Enzymatic digestion | | COR88Ex P3 + 1 MSCs isolated by the explants method | |
|---|---|---|---|---|
| | Non stimulated | Stimulated | Non stimulated | Stimulated |
| Viability | 97.8% | 95.8% | 99.2% | 97.1% |
| Cell count | $6.0 \times 10^6$ | $4.65 \times 10^6$ | $6.2 \times 10^6$ | $8.26 \times 10^6$ |

TABLE 6 molecular markers of umbilical cord-derived MSCs obtained by the two experimental conditions exposed in 2.1. and 2.2.

| | COR27 Enz (−) | COR27 Enz (+) | COR88 Ex (−) | COR88 Ex (+) |
|---|---|---|---|---|
| CD73+ | 100.00% | 99.88% | 99.99% | 99.99% |
| CD90+ | 99.98% | 99.87% | 99.95% | 98.56% |
| CD105+ | 99.99% | 100.00% | 99.99% | 99.99% |
| CD31− | 99.97% | 99.59% | 99.85% | 99.92% |
| CD34− | 93.57% | 93.70% | 99.35% | 97.91% |
| CD45− | 99.92% | 99.94% | 99.96% | 99.98% |
| HLADR− | 100.00% | 100.00% | 99.99% | 99.99% |
| CD106+ | 53.41% | 57.21% | 20.68% | 80.31% |
| CD151+ | 99.99% | 100.00% | 99.99% | 100.00% |
| Nestin+ | 100.00% | 100.00% | 100.00% | 99.98% |

4. Effects of Stimulation with an IL1-IL4 Combination Versus IL1 or IL4 Alone Stimulation on CD106 Levels of Umbilical Cord Mesenchymal Stem Cells Mesenchymal stem cells were isolated from two umbilical cord by explant isolation (see 2.1.).

All cells were cultivated in the same culture medium (αMEM+5% platelet lysate (LP)), stimulated at passage 4 according to the method of the invention with a mix of 10 ng/mL of IL-1b and 10 ng/mL of IL-4, or by each interleukin separately (10 ng/mL each) and collected 2 days after stimulation. Cells viability is measured and cells were counted.

The expression of several phenotypic markers, including CD106, was then measured by flow cytometry.

All MSCs, regardless of the stimulation condition, expressed phenotypic markers in a classical way: CD73, CD90, CD105 are over 95% positive, while CD31, CD34, CD45 and HLA-DR were negative. CD151+ was also over 95% positive, independently of the stimulation.

Regarding the CD106 marker, the increase of expression observed with the stimulation with a combination of IL1 and IL4 is 3 to 5-fold higher than the increase of expression observed with a single interleukin stimulation (see Table 7.).

TABLE 7

CD106 expression levels obtained after stimulation of MSCs with a combination of IL1-IL4 or with a single IL.

| | % of CD106 | |
|---|---|---|
| | CORD 1 | CORD 2 |
| Unstimulated cells | 11.60% | 5.00% |
| IL-1b + IL-4 stimulation | 75.88% | 54.29% |
| IL-1b stimulation | 32.19% | 13.41% |
| IL-4 stimulation | 22.88% | 15.77% |

5. Neovascularization Effect of Placental Derived CD106$^{high}$ CD151+Nestin+ MSCs in Diabetic Rats This example focuses on the therapeutic neovascularization effect of placental derived CD106$^{high}$ CD151+Nestin+ MSCs. It provides insights into their potential for clinical use as a cell-based therapy combined with insulin injection for treating critical hind limb ischemia in diabetes. Our results showed that Placenta derived CD106$^{high}$ CD151+ Nestin+ MSCs participate in angiogenesis and therapeutic vascularisation in order to improve ischemia and restore blood flow perfusion by directly differentiating into vascular cells. In addition, placenta derived CD106$^{high}$ CD151+Nestin+ MSCs improved ischemia damage and functional recovery in diabetic rats.

Immunodeficient male nude rats of six weeks of age were purchased from Vital River Laboratories (Charles River Laboratories suppler in China). Diabetes was induced with a single intraperitoneal injection of streptozotocin (70 mg/kg in Citrate buffer solution, only prepared immediately prior to injection) after overnight fasting. Fasting plasma glucose levels were measured every week and rats with Plasma glucose between 11 mM and 15 mM were considered to be diabetic. Age- and weight-matched nude rats receiving an intraperitoneal citrate buffer injection were used as non-diabetic controls (glycaemia between 5.5 and 8 mM).

Two weeks later, diabetic nude rats were anesthetized (60 mg/kg pentobarbital intraperitoneally) and the left femoral artery were occluded by ligating it with 3-0 silk. The ligature was applied 0.5 cm proximally to the bifurcation of the saphenous and popliteal arteries. Lipiodol (1.5 ml/kg) was used to induce an embolism intravascularly. A sham ligature was applied to the left femoral artery with the left hind limb remaining non ischemic.

After the ischemia model was established, the surgical limb deficiency was obvious as the limb could no longer support any weight and the paw was swollen and red. Over time the ischemic damage improved to different degrees in all the groups. The recovery of limb function was significantly increased in CD106$^{high}$ CD151+Nestin+ MSCs subpopulation (FIG. 4).

Figure 4:
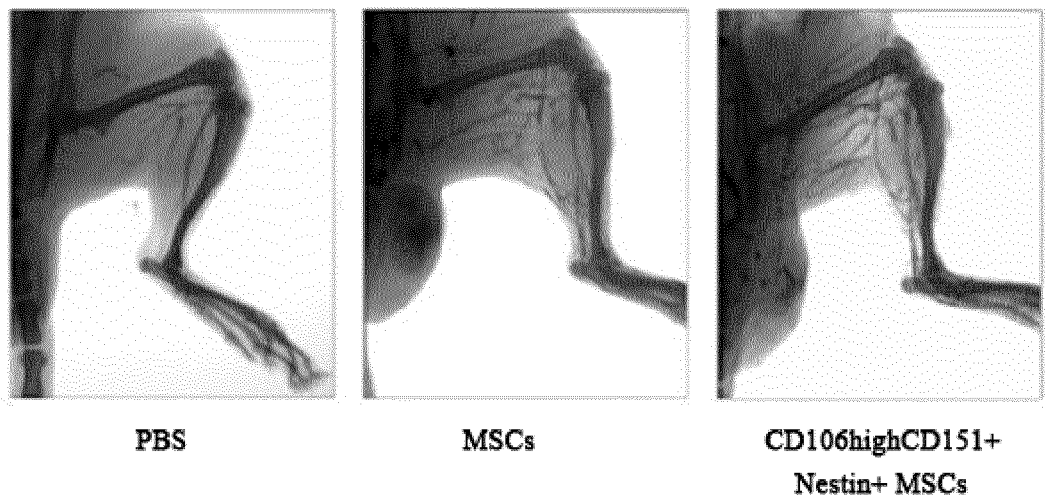
FIG. 4 shows a pathological examination by angiography: Representative angiograms obtained on postoperative day 21.

More precisely, the histological data on FIG. 4 show that the capillary density was increased in the cell transplant groups compared to the PBS group. In addition, more capillary numbers were observed in the CD106$^{high}$ CD151+Nestin+ MSCs subpopulation cell transplant groups in diabetic rats and non-diabetic rats in comparison with the PBS group.

Figure 5:
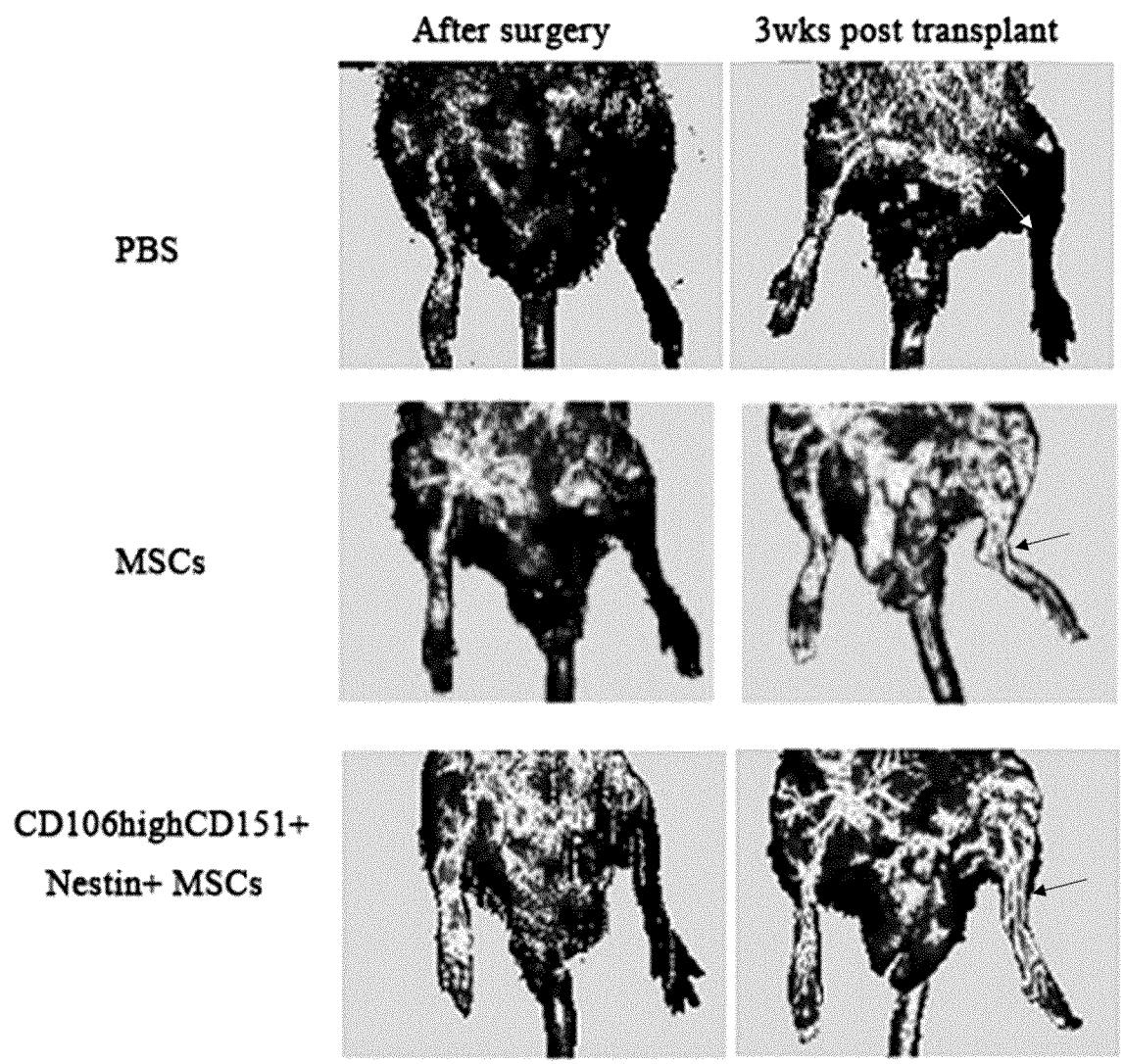
FIG. 5 shows a pathological examination by LDPI: Representative LDPI images obtained on postoperative day 0 and day 21. On the above panel, the area is still affected 3 weeks after the transplant, as shown by the white arrow. On the lower panels, black arrows highlight perfused area, 3 weeks after the transplant.

FIG. 5 showed the functional evidence of ischemia-induced changes using vascularisation LDPI. The image shows that blood flow was completely blocked in the left hind limb on the surgical day; this is indicated by the deep dark colour. Three weeks later, the blood flow perfusion was restored to some degree in all the groups but did not return to normal in the PBS group where the ischemia/non-ischemia perfusion ratio only achieved 52%. The perfusion recovery in the cell transplant groups was significantly higher. The ratio was 81% in the P-MSCs group of the prior art (P<0.05 vs PBS group) and 86% for the $CD106^{high}CD151^+Nestin^+$ MSCs subpopulation group (P<0.01 vs PBS group).

The perfusion recovery in both MSCs subpopulation was significantly higher. Therefore, the results revealed that MSCs improve blood flow perfusion and that the MSCs of the invention are more effective in doing so. In fact, the MSCs of the invention showed a significant improvement in the restoration of blood flow in both diabetic and non-diabetic rats.

The results revealed that the MSCs of the invention improve blood flow perfusion more efficiently than the MSCs of the prior art. This example indicates that administration of the MSCs of the invention is a promising new approach for diabetic critical limb ischemia.

6. Therapeutic Effect of Placenta Derived $CD106^{high}CD151^+Nestin^+$ MSCs of the Invention to Patients with Diabetes This example focuses on the therapeutic effect of placenta derived $CD106^{high}$ $CD151^+Nestin^+$ MSCs of the invention to patients suffering from diabetes. It provides insights into their potential for a clinical use as a cell-based therapy diabetes.

A total of 15 patients with diabetes (11 men and 4 women) were included in this clinical trial. The inclusion criteria were patients with type 2 diabetes diagnosed from November 2013 to November 2014 in Tianjin General Hospital. The patients were between 30 and 85 years of age, duration of diabetes≥3 years, requiring insulin for optimal glycemic control in a dose of ≥0.7 U/kg/day at least for 1.5 year, having insulin dysfunction, poorly controlled blood glucose fluctuation with insulin-based treatment, and willingness to participate in the study. These 15 patients were between 42 and 67 years of age, with a median age of 59 years old; duration of diabetes from 3 years to 17 years, with an median of 8 years; daily insulin requirement from 38 units to 90 units, with an average of 58.7 units. Simultaneous glucose tolerance test, insulin release test, C peptide stimulation test and the determination of glycosylated hemoglobin was examined every three months. The cardiac, liver and kidney function tests were performed. The adverse events and side effects were observed during treatment. It was considered it to be effective if daily insulin requirement reduced by ≥50% after treatment and lasted more than 3 months.

The patients received three intravenous infusions of the placenta derived MSCs (P-MSCs) of the invention, with one month interval of infusion. The total number of P-MSCs administered for each patient was of $(1.0-1.5) \times 10^6$/kg, with an average of $1.25 \times 10^6$/kg. At the same time, patients continued to apply insulin, and adjusted the insulin dose according to blood glucose levels. For complications, the original general treatments were maintained. All of the patients were followed up after therapy for at least 6 months.

This clinical trial showed a reduction in mean insulin requirement after 3 administrations of placenta derived MSCs of the invention in this group of 15 patients, which was statistically significant (P<0.001). The insulin injection dosage for patients with diabetes almost decreased by half after Placenta-derived MSCs of the invention were administered (as compared with the mean insulin dosage taken during the 6 months prior to MSCs administration) (FIG. 6A).

Figure 6:
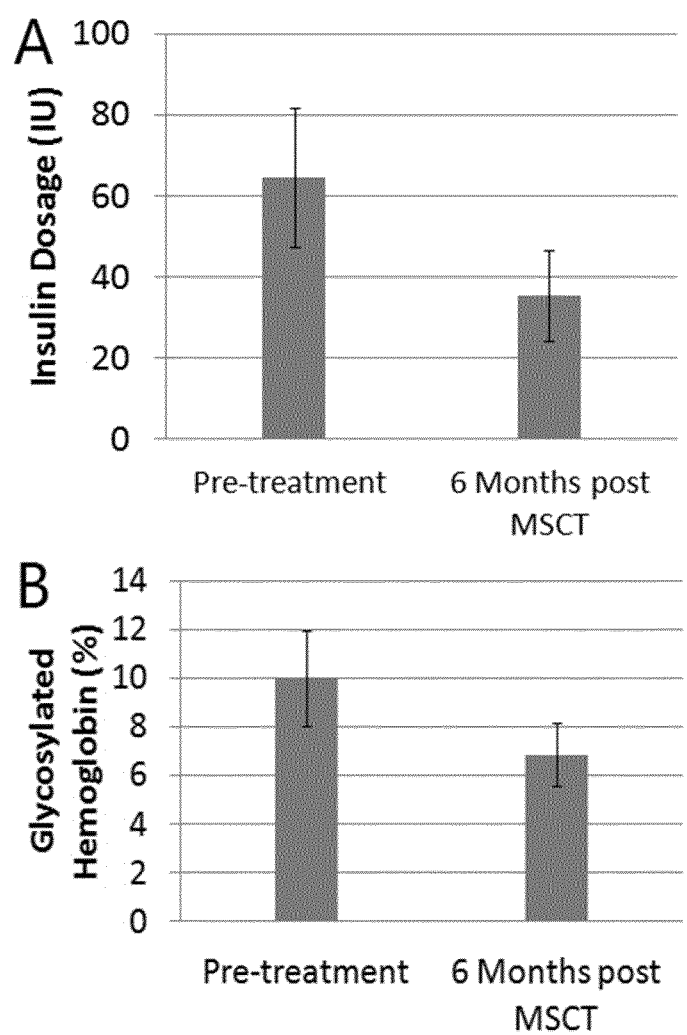
FIG. 6 shows the results of placenta derived MSCs infusion for patients with diabetes. A total of 15 patients with diabetes (11 men and 4 women) were included in this clinical trial. (A) shows a reduction in mean insulin requirement after 3 times of treatment with perinatal tissue derived $CD106^{high}$ $CD151^+Nestin^+$ MSCs in this group of 15 patients, which was statistically significant (P<0.001). (B) shows that the treatment of perinatal derived $CD106^{high}$ $CD151^+Nestin^+$ MSCs also significantly improved the level of glycosylated hemoglobin of patients with diabetes (P<0.001). These results show that perinatal derived $CD106^{high}$ $CD151^+Nestin^+$ MSCs may be a good choice for patients with diabetes.

This clinical trial showed that the treatment with placenta derived MSCs of the invention significantly decreased the level of glycosylated hemoglobin of patients with diabetes (P<0.001) (FIG. 6B).

These data support that the MSCs of the invention can be used for treatment of patients with diabetes.

7. Therapeutic Effect of the Placenta Derived MSCs of the Invention to Patients with Aplastic Anemia This example focuses on the therapeutic effect of placenta derived MSCs of the invention to patients with aplastic anemia and provides insights into their potential for clinical use as a cell-based therapy for aplastic anemia.

Aplastic anemia is mostly considered as an immune-mediated bone marrow (BM) failure syndrome, characterized by hypoplasia and pancytopenia with fatty BM and reduced angiogenesis. Previous investigations have demonstrated that acquired aplastic anemia is manifested by abnormalities of HSCs/HPCs and hematopoietic microenvironment. Lots of evidences have hinted that aplastic anemia might be a syndrome characterized by stem/progenitor-cell disorders including HSCs/HPCs and MSCs. MSCs support hematopoiesis and regulate almost overall immune cells function to maintain the hematopoietic and immune homeostasis. MSCs can modulate the functions of the main immune cell including T cells, B cells, monocytes, DCs, NKTs and neutrophils [5]. MSCs possess remarkable immunosuppressive properties on Th1, Th17 and CTLs. MSCs inhibit the proliferation of T cells, IFN-γ and TNF-α secretion by Th1 cells while promoting IL-10 production by Th2 cells and the expansion of Treg cells. However, recent researches showed that MSCs from aplastic anemia patients had poor proliferation and deficient immune suppression of MLR, PHA-induced T cell activation and IFN-γ release [6, 7]. Our recent study showed that MSCs from aplastic anemia patients were reduced in suppressing the proliferation and clonogenic potential of CD4+ T cells while promoting Treg cells expansion. MSCs were also found defective in suppressing the production of TNF-α and IFN-γ by CD4+ cells. However, there was no significant difference in regulating the production of IL-4, IL-10 and IL-17 [8]. In addition, our research also showed that MSCs from aplastic anemia patients showed aberrant morphology, decreased proliferation and clonogenic potential, and increased apoptosis as compared with BM-MSCs from healthy controls. MSCs from aplastic anemia patients were susceptible to be induced to differentiate into adipocytes but more difficult to differentiate into osteoblasts. Consistent with abnormal biological features, a large number of genes implicated in cell cycle, cell division, proliferation, chemotaxis and hematopoietic cell lineage showed markedly decreased expression in MSCs from these aplastic anemia patients. Conversely, more genes related with apoptosis, adipogenesis and immune response showed increased expression in MSCs from aplastic anemia patients. The gene expression profile of MSCs further confirmed the abnormal biological properties and provided significant evidence for the possible mechanism of the destruction of the BM microenvironment in aplastic anemia [9].

MSCs is a promising therapeutic candidate for treating aplastic anemia due to the following two important facts:
i) the hematopoiesis supportive and potent immunosuppressive capability of MSCs in general and ii) the biological characteristic difference and functional deficiency observed in MSCs derived from patients with aplastic anemia.

In a clinical trial, a 6-year-old girl with intermittent fever continued for more than a month was treated with MSCs. Aplastic anemia was confirmed after two bone marrow biopsies revealed hypocellularity. There was no improvement in the peripheral blood phenotype after treatment of cyclosporine and stanozolol for almost 6 months. Hematopoietic stem cell transplantation was not good choice because it was very difficult to find a matched donor. Therefore, the patient was administered by intravenous infusion with $1\times10^7$ of the placenta derived MSCs of the invention. The peripheral blood phenotype improved significantly after the $1^{st}$ MSCs transplantation. However, the patient was still dependent on blood products transfusion including red blood cell and platelet transfusion. 6 months later, the patient accepted for the $2^{nd}$ time a $1\times10^7$ intravenous injection of the MSCs of the invention. The phenotype of peripheral blood improved significantly and reached almost normal levels 12 months after the $2^{nd}$ injection. In addition, the patient was completely independent on blood products transfusion 12 months after the $2^{nd}$ injection (Table 8). These data support that the placenta derived MSCs of the invention can be used for clinical treatment of patients with aplastic anemia.

TABLE 8

The phenotype of peripheral blood during the treatment of placenta derived MSCs.

| Phenotype of PB | Pre-treatment | 6 months post $1^{st}$ MSCT | 12 months post $2^{nd}$ MSCT |
|---|---|---|---|
| WBC | $0.64 \times 10^9/l$ | $4 \times 10^9/l$ | $5 \times 10^9/l$ |
| ANC | $0.03 \times 10^9/l$ | $1 \times 10^9/l$ | $1.5 \times 10^9/l$ |
| HGB | 48 g/l | 80 g/l | 110 g/l |
| PLT | $3 \times 10^9/l$ | $28 \times 10^9/l$ | $53 \times 10^9/l$ |

8. Therapeutic Effect of the Placenta Derived MSCs of the Invention to Patients with Liver Diseases This example focuses on the therapeutic effect of placenta derived MSCs obtained according to the method of the invention (i.e., with IL1 and IL4 treatment) administered to patients suffering from liver diseases. It provides insights into their potential for clinical use as a cell-based therapy for liver diseases.

In this clinical trial, a 40-year-old man was confirmed suffering from alcoholic hepatitis for more than ten years. The patient was confirmed with decompensated cirrhosis two years ago although he accepted conventional treatment. Because there is no good choice for treatment of decompensated cirrhosis, the patient accepted voluntarily an intravenous injection of $4\times10^7$ MSCs of the invention.

Figure 7:
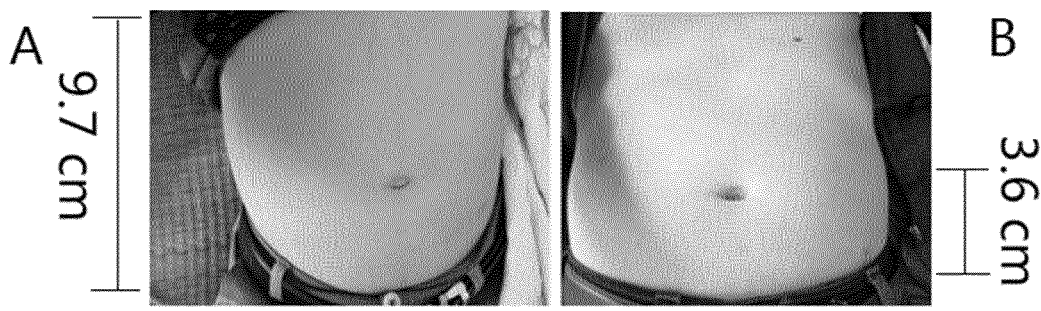
FIG. 7. (A) show the ascites level using ultrasonic examination before $CD106^{high}$ $CD151^+Nestin^+$ MSCs infusion in a patient suffering from decompensated cirrhosis. And (B) show the ascites level using ultrasonic examination one month after the $CD106^{high}$ $CD151^+Nestin^+$ MSCs were administered. (C) show that the liver functions of said patient improved significantly. CA125 expression decreased to normal level. In addition, total protein, albumin, globulin in serum also increased significantly.

In this clinical trial, the ultrasonic examination results showed an ascite level of 9.7 cm before MSCs were administered (see FIG. 7A). However, the ascite level decreased to 3.6 cm one month after the administration of the MSCs (FIG. 7 B). Furthermore, the results showed that the liver functions of patient with decompensated cirrhosis improved significantly after the administration of the MSCs. Moreover, CA125 expression in serum decreased to normal level according to the clinical references.

These results demonstrate the excellent clinical reaction in decompensated cirrhosis patients treated with the MSCs of the invention.

In addition, total protein, albumin, globulin in serum also increased significantly to reach the normal level according the clinical references (FIG. 7 C). These results showed that patient's liver synthetic and metabolic function improved one month after the intravenous injection of MSCs.

Therefore, the placenta derived MSCs of the invention is a very good cytotherapeutic choice for liver diseases.

9. Angiogenic Potential of the Cells of the Invention, Obtained from Umbilical Cord The pro-angiogenic potential of the MSC of the invention has been further tested in a hindlimb ischemia murine model.

Material & Methods

Twelve 8-week-old NOD/SCID mice (Laboratoire Janvier) were anesthetized with a mix of ketamin and xylazine. The left proximal and distal parts of the femoral artery of the left leg was then ligated (6.0 silk suture, Ethicon, Issy-Les-Moulineaux, France) and the part between ligations excised. Mice that exhibit more than 80% of ischemia after surgery were intramuscularly injected in the gastrocnemius muscle of the ischemic limb with 2 doses of MSCs of the invention as obtained according to the protocols exposed in point 2.4. above ($0.5\times10^6$ cells per animal in Group 2, $0.05 \cdot 10^6$ cells per animal in Group 3). A saline solution injection was used in the Control Group 1. A dose of 20 ng/mL of VEGF/mice was also injected in the Control Group 4.

The injection scheme as well as the dose was derived for the intended clinical use of the cells and the dose administered to animals was >10 times the proposed dose for a phase I/II clinical trial in humans (which is of about $25\times10^6$ cells/kg, that means about $0.5\times10^6$ cells/mouse (average mouse weight=20 gr)).

Hind limb blood flow was measured using a scanner-laser Doppler (Laser Doppler Perfusion system, Perimed PeriScan PIM III). The average perfusion of ischemic and non-ischemic limbs was determined before and after ischemia, and every 7 days until 21 days after ischemia. Blood flow-dependent changes in laser frequency were imaged using different colored pixels. Images were analyzed to quantify blood flow by using a blood perfusion analysis software (LPDIwin). Percentage of perfusion was expressed as the ratio of the ischemic to the non-ischemic hind limb.

Hematoxylin-Eosin Staining of Hind Limb Muscle Sections

Mice were euthanized at the end of the experiment (D21). Hind-limb gastrocnemius muscles were dissected and stained to visualize the distribution of the cells nuclei in the muscular fiber. Muscles isolated from the ischemic hind limb were fixed in paraffin and stained with hematoxylin/eosin.

Results

Figure 8:
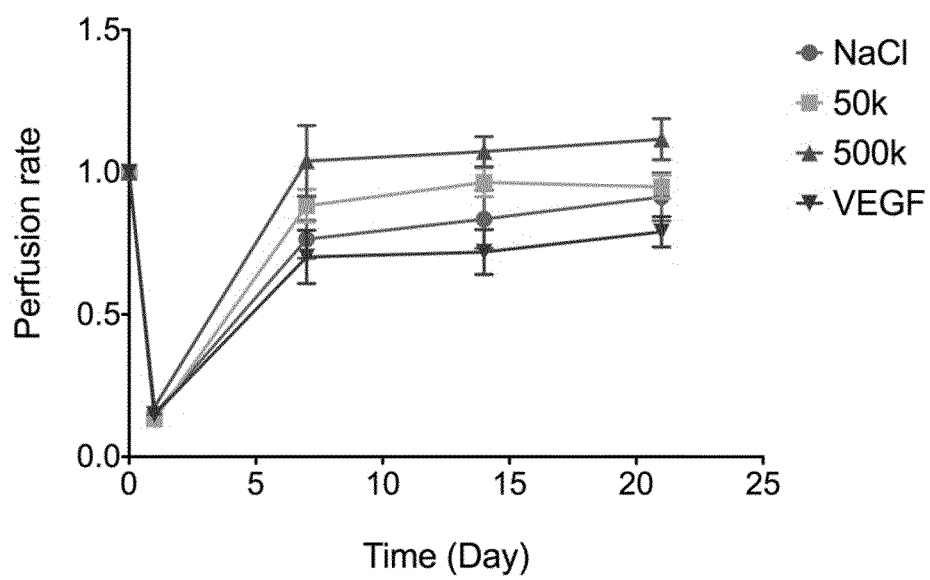
FIG. 8 shows the evaluation of the perfusion rate in a NOD/SCID mouse hindlimb ischemia model after arterial ligation and injection of various doses of umbilical cord MSCs of the invention, or saline solution or VEGF.

FIG. 8 shows the mean reperfusion rate after hind limb ischemia in mice treated with different injections: NaCl 0.9% (negative control—n=8), VEGF 20 ng/ml (positive control—n=6), $50 \cdot 10^3$ MS cells (n=9) and $500 \cdot 10^3$ MS cells (n=7).

These results demonstrated that administration of high doses of the MSCs of the invention in mice after ligation of the femoral artery resulted in higher perfusion rates when compared to vehicle (NaCl) of VEGF administered alone. A 100% perfusion rate was observed as early as 7 days post cell injection for mice receiving the highest dose of cells ($0.5\times10^6$ cells). There was a statistically significant difference with the other groups.

Also, a dose response effect is likely since in this preliminary experiment the highest dose of cells ($0.5 \times 10^6$ cells) seems to achieve better perfusion rate than a 10 folds lower dose.

These results confirm the actual angiogenic potency of the MSCs of the invention to improve blood perfusion in this mouse model of CLI.

Results Observed in the Hematoxylin-Eosin Staining (Data Not Shown):

In the normal, non-ischemic muscles, cells nuclei are distributed in the periphery of the muscular fiber.

In the ischemic muscles of mice from Groups 1 (NaCl 0.9%) and 4 (VEGF 20 ng/mL), 21 days after ischemia induction, cells exhibit very few nuclei in the periphery of the muscular fiber, since they are still regenerating.

In the ischemic muscles of mice from Group 3 ($0.05 \cdot 10^6$ MSC cells or 50 k), 21 days after ischemia induction, 50% of muscular fibers are regenerated and exhibit nuclei in the periphery of the fiber. The regeneration happens faster than in Groups 1 and 4.

In the ischemic muscles of mice from Group 2 ($0.5 \times 10^6$ MSC cells or 500 k), 21 days after ischemia induction, 100% of muscular fibers are regenerated and exhibit nuclei in the periphery of the fiber. The staining profile of the muscle is identical to the normal, non-ischemic, muscle. In this experiment, the 500 k cells dose allows a complete regeneration of the muscle.

BIBLIOGRAPHIC REFERENCES

1. Shi M, Zhang Z, Xu R, Lin H, Fu J, Zou Z, Zhang A, Shi J, Chen L, Lv S et al: Human mesenchymal stem cell transfusion is safe and improves liver function in acute-on-chronic liver failure patients. *Stem cells translational medicine* 2012, 1(10):725-731.
2. Wang L, Wang L, Cong X, Liu G, Zhou J, Bai B, Li Y, Bai W, Li M, Ji H et al: Human umbilical cord mesenchymal stem cell therapy for patients with active rheumatoid arthritis: safety and efficacy. *Stem cells and development* 2013, 22(24):3192-3202.
3. Rodrigo S F, van Ramshorst J, Hoogslag G E, Boden H, Velders M A, Cannegieter S C, Roelofs H, Al Younis I, Dibbets-Schneider P, Fibbe W E et al: Intramyocardial injection of autologous bone marrow-derived ex vivo expanded mesenchymal stem cells in acute myocardial infarction patients is feasible and safe up to 5 years of follow-up. *Journal of cardiovascular translational research* 2013, 6(5):816-825.
4. Gupta P K, Chullikana A, Parakh R, Desai S, Das A, Gottipamula S, Krishnamurthy S, Anthony N, Pherwani A, Majumdar A S: A double blind randomized placebo controlled phase I/II study assessing the safety and efficacy of allogeneic bone marrow derived mesenchymal stem cell in critical limb ischemia. *Journal of translational medicine* 2013, 11:143.
5. Chen X, Armstrong M A, Li G: Mesenchymal stem cells in immunoregulation. *Immunology and cell biology* 2006, 84(5):413-421.
6. Bacigalupo A, Valle M, Podesta M, Pitto A, Zocchi E, De Flora A, Pozzi S, Luchetti S, Frassoni F, Van Lint M T et al: T-cell suppression mediated by mesenchymal stem cells is deficient in patients with severe aplastic anemia. *Experimental hematology* 2005, 33(7):819-827.
7. Chao Y H, Peng C T, Ham H J, Chan C K, Wu K H: Poor potential of proliferation and differentiation in bone marrow mesenchymal stem cells derived from children with severe aplastic anemia. *Annals of hematology* 2010, 89(7):715-723.
8. Li J, Lu S, Yang S, Xing W, Feng J, Li W, Zhao Q, Wu H, Ge M, Ma F et al: Impaired immunomodulatory ability of bone marrow mesenchymal stem cells on CD4(+) T cells in aplastic anemia. *Results in immunology* 2012, 2:142-147.
9. Li J, Yang S, Lu S, Zhao H, Feng J, Li W, Ma F, Ren Q, Liu B, Zhang L et al: Differential gene expression profile associated with the abnormality of bone marrow mesenchymal stem cells in aplastic anemia. *PloS one* 2012, 7(11):e47764.
10. Anna Otte, Vesna Bucan, Kerstin Reimers, and Ralf Hass. Mesenchymal Stem Cells Maintain Long-Term In Vitro Stemness During Explant Culture. *Tissue Engineering Part C: Methods*. November 2013, 19(12): 937-948
11. Van Pham, P., Truong, N. C., Le, P. T B. et al. Isolation and proliferation of umbilical cord tissue derived mesenchymal stem cells for clinical applications. *Cell Tissue Bank* (2016) 17: 289
12. Dong Li et al, Biological characteristics of human placental mesenchymal stem cells and their proliferative response to various cytokines. *Cells Tissues Organs* 2007; 186:169-179.
13. Abomaray F. M. et al, Phenotypic and functional characterization of mesenchymal stem/multipotent Stromal cells from Decidua Basalis of human term placenta. *Stem cells international, volume* 2016, Article ID5184601
14. Savilova A. M. et al, Comparison of the expression of immunomodulatory factors in cultures of mesenchymal stromal cells from human extraembryonic tissues. *Cell Technologies in Biology and Medicine, No* 4, February 2015
15. Hongye Fan et al, Pre-treatment with IL-1β enhances the efficacy of MSC transplantation in DSS-induced colitis. *Cellular and Molecular Immunology* (2012), 9, 473-481
16. Han Z. C., et al, New insights into the heterogeneity and functional diversity of human mesenchymal stem cells. *Bio-medical Materials and Engineering* 28 (2017) S29-S45
17. Du W. et al, VCAM-1+ placenta chorionic villi-derived mesenchymal stem cells display potent pro-angiogenic activity. *Stem Cell research & therapy* (2016) 7:49

The invention claimed is:

1. A method for obtaining CD106+CD151+Nestin+mesenchymal stem cells (MSCs), said method comprising:
   culturing a population of undifferentiated MSCs in a first culture medium devoid of any exogenous growth factor until said undifferentiated MSCs reach 85-90% confluence,
   removing the first culture medium,
   introducing a second culture medium to the culture of undifferentiated MSCs comprising between 10 and 20 ng/ml of added Interleukin 1β and between 10 and 20 ng/ml of added Interleukin 4,
   culturing said undifferentiated MSCs in the second culture medium for at least 48 hours to obtain CD106+CD151+Nestin+MSCs, and
   characterizing the CD106+CD151+Nestin+MSCs based on marker expression,
   wherein over 60% of the CD106+CD151+Nestin+MSCs express CD106 at a detectible level,
   wherein over 98% of the CD106+CD151+Nestin+MSCs express CD151 at a detectible level,
   wherein over 98% of the CD106+CD151+Nestin+MSCs express Nestin at a detectible level
   wherein over 95% of the CD106+CD151+Nestin+MSCs express CD73, CD90, CD105, and CD166 at a detectible level, and
   wherein less than 2% of the CD106+CD151+Nestin+MSCs express CD45, CD34, and HLA-DR at a detectible level.

2. The method of claim 1, wherein said undifferentiated MSCs are obtained by cell isolation from an explant of umbilical cord fragment or by cell isolation from a placenta tissue fragment.

3. The method of claim 1, wherein over 98% of the MSCs do not express markers CD11b, CD14, CD15, CD16, CD31, CD34, CD45, CD49f, CD102, CD104, and CD133 at a detectible level.

4. A method for enhancing the CD106 expression level of undifferentiated CD106+CD151+Nestin+mesenchymal stem cells (MSCs), said method comprising:
   culturing a population of undifferentiated MSCs in a first culture medium devoid of any exogenous growth factors until said undifferentiated MSCs reach 85-90% confluence,
   removing the first culture medium,
   introducing a second culture medium to the culture of undifferentiated MSCs comprising between 10 and 20 ng/ml of added Interleukin 1β and between 10 and 20 ng/ml of added Interleukin 4,
   culturing said undifferentiated MSCs in the second culture medium for at least 48 hours to produce undifferentiated CD106+CD151+Nestin+MSCs, and
   characterizing the CD106+CD151+Nestin+MSCs based on marker expression,
   wherein the CD106 expression is enhanced such that over 60% of the undifferentiated CD106+CD151+Nestin+MSCs express CD106 at a detectible level,
   wherein over 98% of the undifferentiated CD106+CD151+Nestin+MSCs express CD151 at a detectible level,
   wherein over 98% of the undifferentiated CD106+CD151+Nestin+MSCs express Nestin at a detectible level,
   wherein over 95% of the undifferentiated CD106+CD151+Nestin+MSCs express CD73, CD90, CD105, and CD166 at a detectible level, and
   wherein less than 2% of the undifferentiated CD106+CD151+Nestin+MSCs express CD45, CD34, and HLA-DR at a detectible level.

5. The method of claim 4, wherein said undifferentiated MSCs are obtained by cell isolation from a placenta tissue fragment.

6. The method of claim 4, wherein over 98% of the MSCs do not express markers CD11b, CD14, CD15, CD16, CD31, CD34, CD45, CD49f, CD102, CD104, and CD133 at a detectable level.

7. A method for obtaining CD106+CD151+Nestin+mesenchymal stem cells (MSCs), comprising the steps of:
   a) collecting mononuclear cells contained in a perinatal biological tissue or fluid,
   b) culturing the mononuclear cells in a first culture medium devoid of any exogenous growth factor, wherein said mononuclear cells are passaged when they reach 85-90% confluence,
   c) characterizing the mononuclear cells based on marker expression to obtain a population of undifferentiated MSCs, wherein 95% of the undifferentiated MSCs express the markers CD73, CD90, CD105 and CD166, and less than 2% express the markers CD45, CD34 and HLA-DR,
   d) seeding the population of undifferentiated MSCs obtained from step c) at a density of 1000 to 5000 MSCs per cm2 into a second culture medium,
   e) once the population of undifferentiated MSCs in step d) reaches 40-50% confluency, adding between 10 and 20 ng/ml of Interleukin 1β and between 10 and 20 ng/ml of Interleukin 4, and culturing said population of undifferentiated MSCs for at least 48 hours,
   f) collecting the population of undifferentiated MSCs from step e) when they reach 90-95% confluence,
   g) characterizing the population of undifferentiated MSCs obtained from step f) based on expression of markers comprising CD106, CD151, and Nestin to obtain a population of CD106+CD151+Nestin+MSCs,
   wherein the CD106 expression is enhanced such that over 60% of the undifferentiated CD106+CD151+Nestin+ MSCs express CD106 at a detectible level,
   wherein over 98% of the undifferentiated CD106+CD151+Nestin+MSCs express CD151 at a detectible level,
   wherein over 98% of the undifferentiated CD106+CD151+Nestin+MSCs express Nestin at a detectible level.

8. The method of claim 7, wherein over 98% of the MSCs do not express markers CD11b, CD14, CD15, CD16, CD31, CD34, CD45, CD49f, CD102, CD104, and CD133 at a detectable level.

* * * * *